United States Patent
Forsell et al.

(10) Patent No.: US 10,301,052 B2
(45) Date of Patent: May 28, 2019

(54) METHOD FOR PREPARING MAMMALIAN TISSUE FOR STORAGE, IMPLANT, AND TRANSPLANT

(71) Applicants: James H. Forsell, San Raphael, CA (US); Gerald John Cole, Baltimore, MD (US); Jeffrey Dow Holiman, Portland, OR (US)

(72) Inventors: James H. Forsell, San Raphael, CA (US); Gerald John Cole, Baltimore, MD (US); Jeffrey Dow Holiman, Portland, OR (US)

( * ) Notice: Subject to any disclaimer, the term of this patent is extended or adjusted under 35 U.S.C. 154(b) by 23 days.

(21) Appl. No.: 15/452,844

(22) Filed: Mar. 8, 2017

(65) Prior Publication Data

US 2017/0203002 A1 Jul. 20, 2017

Related U.S. Application Data

(63) Continuation-in-part of application No. 14/314,084, filed on Jun. 25, 2014, now abandoned.

(60) Provisional application No. 61/839,041, filed on Jun. 25, 2013.

(51) Int. Cl.
  *B65B 63/08* (2006.01)
  *A61L 27/36* (2006.01)
  *A61L 2/00* (2006.01)
  *B65B 55/16* (2006.01)

(52) U.S. Cl.
  CPC .............. *B65B 63/08* (2013.01); *A61L 2/007* (2013.01); *A61L 27/3633* (2013.01); *A61L 27/3691* (2013.01); *B65B 55/16* (2013.01); *A61L 2202/23* (2013.01); *A61L 2430/16* (2013.01)

(58) Field of Classification Search
  CPC ......... B65B 2220/18; B65B 5/04; B65B 7/02; B65B 1/20; B65B 65/006; B65B 35/04; B31B 2170/20; B29C 48/08; B29C 48/21; B32B 15/20; B32B 2439/80; H01L 2924/01013; B01L 2300/0887
  See application file for complete search history.

(56) References Cited

U.S. PATENT DOCUMENTS

| | | | |
|---|---|---|---|
| 2003/0031581 A1* | 2/2003 | Miekka | A23L 3/263 422/1 |
| 2003/0211261 A1* | 11/2003 | Phillips | B32B 27/06 428/35.7 |
| 2007/0224587 A1* | 9/2007 | Forsell | A01N 1/02 435/1.1 |
| 2012/0125798 A1* | 5/2012 | Baecker | A61F 15/001 206/524.1 |

FOREIGN PATENT DOCUMENTS

EP   1637037   *   3/2006   .............. A01N 1/00

OTHER PUBLICATIONS

Daoud et al. The intraoperative impression and postoperative outcomes of gamma-irradiated corneas in corneal and glaucoma patch surgery. Cornea. 2011;30:1387-1391.*
He et al. Large-scale production of functional human serum albumin from transgenic rice seeds. PNAS. 2011;108(47):19078-19083.*
EBAA . Medical standards. EBAA. 2011;1-46.*

* cited by examiner

*Primary Examiner* — Lynn Y Fan
(74) *Attorney, Agent, or Firm* — Nadya Reingand

(57) ABSTRACT

The present disclosure relates to methods and systems for processing isolated mammalian tissue for use in surgical grafting, implantation, or transplantation procedures. The method employs electron beam sterilization, the collagen tissue is partially submerged in rHSA (Recombinant Human Serum Albumin), the tissue is stored in specially designed packaging, and the tissue is stored at ambient temperatures without requiring refrigeration. The terminal sterilization using electronic beams takes place in the special packaging. This inventive technology offers advantages including being biologically safe, maintaining tissue integrity while minimizing size, increasing scalability, increasing shelf life, increasing the amount of tissue usable for transplantation, and reducing of costs associated with processing and storing tissue for long periods of time.

15 Claims, 15 Drawing Sheets

| ID | Type | HSA | Volume | Age at Start |
|---|---|---|---|---|
| (illegible) | Full Full | 15% | 400 μL | 10 months |
| (illegible) | Full Full | 15% | 400 μL | 10 months |
| (illegible) | Full Half | 15% | 200 μL | 10 months |
| (illegible) | Full Half | 20% | 200 μL | 10 months |
| (illegible) | Full Half | 15% | 200 μL | 10 months |
| (illegible) | Full Half | 20% | 200 μL | 10 months |
| (illegible) | Full Half | 15% | 200 μL | 10 months |
| (illegible) | Full Half | 20% | 200 μL | 10 months |

FIG. 4

METHOD FOR PREPARING MAMMALIAN TISSUE FOR STORAGE, IMPLANT, AND TRANSPLANT

CROSS-REFERENCE TO RELATED APPLICATIONS

The present application is a Continuation-In-Part of U.S. patent application Ser. No. 14/314,084, filed Jun. 25, 2014, which claims priority to and incorporates fully by reference U.S. Provisional Patent Application Ser. No. 61/839,041, filed Jun. 25, 2013. Both related disclosures are incorporated herein by reference in their entireties.

FIELD OF THE INVENTION

The present invention relates to a method for processing isolated mammalian collagen tissue, and particularly mammalian corneal tissue, for use in surgical grafting, implantation, or transplantation procedures.

BACKGROUND OF THE INVENTION

Doctors have long been using organ and tissue transplantation to treat certain medial conditions. One example of tissue transplants is corneal tissue allografts. Corneal tissue allografts have been successfully conducted since 1905. Today, corneal tissue transplantation is used to treat poor vision due to corneal perforation, infection, scarred tissue as well as complications from cataract surgery and other medical conditions. There are two basic categories of corneal tissue transplants, those that require endothelial cells and those that do not. The corneal endothelium is a thin cell layer on the posterior surface of the cornea. This layer allows transport of solutes and nutrients of the aqueous humor into the cornea while pumping water out of the stroma to the aqueous humor. As a result of such functioning, it follows that one of the primary outcomes of a properly functioning endothelial cell layer is the maintenance of a clear cornea. The present invention discloses a novel and more cost-effective manner through which a substantially similar result (i.e. a clear cornea) is achievable without requiring the transplantation, preservation, or storage of actual endothelial cells.

Some medical conditions, including those where the endothelium is diseased or damaged, require that a viable endothelial layer be transplanted as well as the rest of the corneal tissue. There are situations, however, where the patient's endothelial layer may remain intact and only a portion of the corneal tissue allograft is necessary. Some examples include corneal scars, certain corneal dystrophies, ocular surface deficiencies, chemical or surgical burns and keratoconus. Based on information reported by the Eye Bank Association of America in its 2012 EBAA Annual Statistics Report, about 20% of over 68,000 corneal tissues provided for transplantation from its member eye banks use corneal tissues without the endothelium. In addition, there are some other ocular procedures where a structural or tectonic graft is necessary such as corneal perforations and pterygiums where corneal tissue material is used to patch a patient's compromised surface tissue.

Traditional corneal tissue processing methods seek to preserve the donor corneal tissue by using an organ culture based media in combination with other additives and antibiotics. These corneal tissue storage media, principally Optisol GS (Bausch & Lomb, Costa Mesa, Calif.), can maintain corneal tissue viability for up to fourteen days in combination with refrigeration. With the passage of time, the corneal tissue becomes edematous, loses its transparency and, ultimately, becomes unsuitable for transplantation. There are some known alternatives to cold storage of corneal tissue in preservation media used for tectonic applications. Some of these methods include warm temperature organ culture media, glycerol and alcohol preservation of corneas as well as gamma irradiation. Depending on the method applied, these methods may lack adequate levels of sterility, compromise the corneal stromal matrix, compromise the corneal clarity, and compromise the corneal elasticity or some combination thereof.

One existing method for sterilizing and storing corneal tissue that does not require the endothelial layer remain intact or viable is called Visiongraft and is described in "The Intraoperative Impression and Postoperative Outcomes of Gamma Irradiated Corneas in Corneal and Glaucoma Patch Surgery" (Yassine Daoud et al., 30 CLINICAL SCIENCE 12, 1387-91 (December 2011). There are numerous problems associated with the Visiongraft process. The Visiongraft process uses plasma derived human serum albumin (pdHSA). Human plasma is a complex material composed of hundreds of biochemical entities. Albumin is the most concentrated entity (40,000 mg/liter) in human serum. Typically, pdHSA is not obtained from a single donor but generated as a pool of albumin from multiple paid donors. The ramification of this is that there exists a lot to lot variability that may affect performance. The variability is addressed by the use of recombinant albumin. Human plasma products have the ability to transmit infectious agents such as HIV, HBV, HCV, HAV, HEV, HGV, TT virus, and Parvovirus B19 [World Health Organization, WHO Recommendations for the Production, Control and Regulation of Human Plasma for Fractionation (October 2005)]. Human plasma may also contain mycoplasma and prions.

The Visiongraft process also sterilizes the cornea tissue using gamma irradiation. Gamma irradiation is typically conducted using a Cobalt 60 source. The gamma source, however, generates heat in the environment that will increase the temperature within the exposure chamber. Typically, the gamma source will be exposed to the irradiation chamber (raised out of its water environment) most of the working day, which causes a buildup of heat. Since corneal tissue may be damaged by heat and irradiation, both must be controlled and kept to a minimum.

Gamma radiation can penetrate through 2-3 inches of lead shielding. Thus, due to gamma's penetration ability products of all types are exposed to gamma rays in a 3 dimensional arrangement (containers) on conveyor belts in order to maximize throughput at the gamma facility. This use of 3 dimensional arrangements is not optimal for corneal tissue as it is difficult to obtain a uniform dose throughout the container. Gamma radiation also poses a potential risk to those workers who operate the gamma radiation facility. Overall, gamma radiation is expensive due to the necessary shielding for employees because of the deeply penetrating gamma rays, long exposure time due to the dose rate, inability to turn off the fuel rods, as well as the cost of final storage and disposition of spent fuel rods.

The Visiongraft process also requires that the corneal tissue be fully submerged in storage media in a glass vial. Fully submersing corneal tissue into media in a glass vial makes the identification of clear tissue, such as corneal tissue, significantly harder. The cost of the extra pdHSA required to fill such a prior art vial is also a concern. The corneal tissue needs to be adequately soaked to remove all residual media that may have saturated the transplant tissue.

In addition, glass vials, after exposure to gamma radiation, will turn brown. This browning makes it even more difficult to view the transparent tissue inside the storage container, which will create problems in ensuring adequate quality control during tissue release and tissue location/removal at surgery. Additionally, glass vials can break or leak during transport or in hospital surgical suites during an operation, causing potential harm to both those handling the tissue as well as the tissue itself. Breakage or leakage can also lead to a delay of the surgical procedure as well as upcharges to the patient.

The danger of transferring the infectious agents (such as HIV, HBV, HCV, HAV, REV, HGV, TT virus, Parvovirus B19, mycoplasma and prions) with the donor pdHSA prompted development of rHSA (Recombinant Human Serum Albumin), which is free from the respective pathogens. Such formulations are disclosed in US 2005/0281861 A1 (Hughes et al.) in which rHSA, eye and sterilization are mentioned. However, this is a drug delivery system. The implant is an intravitreal or interocular implant and is a polymer, not a collagenous biological tissue.

The human cornea has 5 layers. Moving anterior to posterior, there exists: (1) Corneal epithelium (the outermost layer of the cornea), (2) Bowman's membrane (a membrane between the epithelium and the corneal stroma), (3) Corneal stroma (the largest/thickest layer of the cornea), (4) Descemet's membrane (membrane between the stroma and the corneal endothelium), and (5) Corneal endothelium (innermost layer of the corneal containing living endothelial cells).

Approximately 70 to 75% of corneal blindness is due to a compromised endothelial cell layer (either by disease or eye trauma). In such cases, an endothelial cell layer transplant or, more often, a posterior cornea transplant with a viable endothelium is required. Most eye bank corneal storage methods and media intend to preserve the viable endothelial cells, which are required for surgeries such as those above. In contrast to such processes and techniques, the present invention is a method to preserve the corneal stromal matrix of the cornea (i.e. Para. 11, item 3, above). The endothelium and epithelium is removed or rendered inactive, as neither is required according to the present invention and its applications. Thus, the focus of the present invention is the processing, packaging, sterilizing, and storing of non-viable, native corneal stromal matrix transplants and/or implants.

SUMMARY OF THE INVENTION

The present invention comprises methods, systems, and packages for preparation and storage of mammalian collagen tissue for transplantation or implantation into a recipient. The inventive method comprises the following steps: (1) receiving a mammalian collagen tissue, said tissue being sufficiently clear based on an evaluation, (2) packaging said mammalian collagen tissue with a medium in a first container, said medium comprising at least 20% recombinant human serum albumin by weight, said medium maintaining said tissue's consistency, said tissue's pliability, and said tissue's clarity, said medium having a total volume of up to 5 milliliters, wherein said mammalian collagen tissue is submerged in said medium, (3) packaging said tissue in said medium in said first container within a second container, (4) electron beam sterilizing said mammalian collagen tissue packaged in said first and second containers, and (5) storing said sterilized mammalian collagen tissue packaged in said first and second containers at an ambient temperature, said storing occurring for up to two years.

In some aspects, said tissue remains partially submerged in said medium.

In some aspects, said mammalian collagen tissue is a human collagen tissue. In some aspects, said human collagen tissue is a corneal tissue. In some aspects, said corneal tissue is a corneal stromal matrix.

In some aspects, said first container further contains an absorbent material.

In some aspects, said electron beam sterilization is conducted at or below an ambient temperature.

In some aspects, said electron beam sterilization delivers an electron beam sufficient for a tissue internal dose of 15 to 25 kilogray (kGy) for a period no greater than 25 minutes from entering the irradiation vault to exiting the irradiation vault. In some aspects, more than one tissue in a package are irradiated in a single file arrangement, said arrangement moving through an EBS chamber.

In some aspects, a transparency of the first and second containers does not change after said electron beam sterilization.

In some aspects, the pouch comprises clear protective barrier films, said films being aluminum oxide coated polyester-based films. In some aspects, said first container is a Nalgene vial. In some aspects, said first container is a clear pouch.

In some aspects, method further comprises splitting said received mammalian collagen tissue into four (4) or more grafts, each graft forming a separate unit to be individually packaged in said packaging step.

In some aspects, said medium has a total volume of about 300 microliters. In some aspects, said medium has a total volume of at least 300 microliters.

In some aspects, the method further comprises freeze-storing said tissue packaged within said first and second containers at a temperature of −40 to −85 degrees Celsius, said freeze-storing occurring after said packaging and before said sterilization.

In some aspects, said electron beam sterilizing comprises irradiating a plurality of thawed tissues, each thawed tissue comprising said tissue packaged within said first and said second containers.

In some aspects, said first container comprises a funnel-shaped reservoir.

In some aspects, said first container further comprises foil. In some aspects, said second container further comprises foil.

BRIEF DESCRIPTION OF THE DRAWINGS

The drawings described herein are for illustrative purposes only and are of selected embodiments not including all possible implementations. The drawings are not intended to limit the scope of the present disclosure, and the figures may not show all elements of particular embodiments, even if operation would be possible without such elements.

The various cross sections shown and described are displayed in various manners, which help to distinguish one part of the invention from others. No illustration herein, however, is used to indicate the nature of the material from which these parts are made.

FIG. 4 is a table detailing various allografts which were prepared and tested for applicability with the present invention. The table provides details for particular samples shown in FIG. 5 in order to further clarify and describe the experimental evidence illustrated and discussed herein.

DETAILED DESCRIPTION OF THE PREFERRED EMBODIMENT

Figure 1:
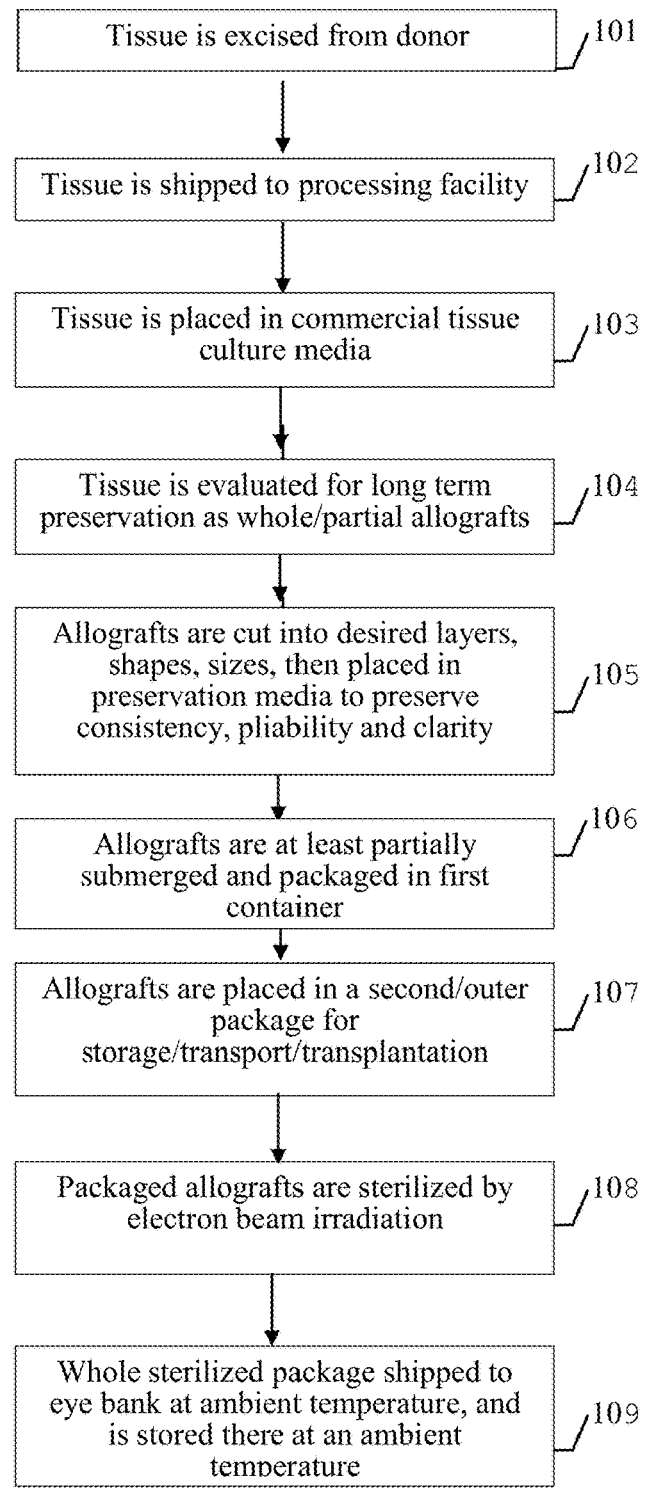
FIG. 1 shows an exemplary embodiment of the processing method according to the present invention.

The present invention comprises a method for preparation, packaging, sterilization, and storage/preservation of isolated mammalian collagen tissue, in particular human corneal tissue for transplant.

Definitions

As used herein, the term "tissue" refers to a functional group of cells in their matrix, layers of cells associated with their matrix, a cell matrix, or organs (including but not limited to soft tissue). As used herein, "corneal tissue" refers to the entire cornea, the cornea without one or more cell layers including the endothelial layer, or the corneal stromal matrix. As used herein, the term "collagen" refers to a fibrous protein constituent of bone, cartilage, tendon, and other connective tissue found in mammals in any amount and in any combination including Collagen Types I, II, III, IV, V, VI, VII, VIII, IX, X, and XI.

Furthermore with regard to the term "tissue," as used herein, it is noted that although the present invention may be used with any mammalian tissue, it is particularly applicable to the storage of tissue having a similar attributes to the human cornea. The media used by the presently disclosed method maintains clarity, among other features, of the tissue as clear or unchanged as in the human cornea. The corneal application of the present method is thus unique because most other tissues are not clear. Other tissues in mammalian species have translucent and/or thin tissues, and may be stored using a similar method; however, none are as clear and transparent as the cornea.

As used herein, the term "irradiate" or "irradiation" refers to any exposure to any high energy generating source that can be used to reduce bioburden, crosslink, or sterilize unless otherwise specified.

As used herein, the term "bioburden/microorganisms" refers to any aerobic bacteria, anaerobic bacteria, fungus, or parasite.

As used here, the term "SAL" refers to the Sterility Assurance Level or the statistical reliability that no microorganisms will be alive on a given sample.

As used herein, the term "sterilize" refers to a reduction of bioburden to a SAL of 1 in 1,000,000 or 10-6. Alternatively, "sterile" may refer to a reduction of 10-5 or 1 in 100,000, 10-4 or 1 in 10,000 or 10-3 or 1 in 1,000.

As used herein, the terms "vial" and "pouch" refers to any container with or without a seal. In the preferred embodiment, the packaging system includes an inner sterilization peel pouch inside an outer sterilization peel pouch. In one embodiment, the inner pouch is a Nalgene vial. It is noted that the vial, in whatever form, is sealed prior to sterilization and opened once only at the time that the tissue is used. It is further noted that the term, "commercially purchased vial," as used herein, refers to a comparable prior art container and not the "vial" or "pouch" of the present invention, as defined in this paragraph.

As used herein, the term "absorbent material" refers to any substance that is inert, wicks moisture and does not deteriorate after irradiation. The term also refers to any material that may be used in the packaging system that is biocompatible with collagen, resistant to irradiation damage, or helps maintain the natural curvature of corneal tissue.

As used herein, the term "ambient temperature" is defined as typical indoor room temperature in which staff may work comfortably for extended periods of time. Typically, the ambient temperature range comprises about 13 degrees Celsius to 30 degrees Celsius, or more preferably from 15 degrees Celsius to 26 degrees Celsius. It is further noted that all long term storage conditions, as discussed herein, should be in an indoor, secure/controlled access location. In contrast, any non-ambient temperature that the tissue may be exposed to during shipment, irradiation, or processing should have additional specified guidance as to the required conditions for each stage, e.g., in refrigeration, frozen, cooled, or in validated packaging for shipping to protect against high and low temperature extremes for any shorter periods prior to and during the sterilization step.

As used herein, the term "transplantation" refers to the removal or transfer of tissue from one organism to a recipient within the same species (allograft) or between different species (xenograft). As used herein, the term "implantation" refers to the addition of tissue to one recipient from the tissue of another organism (donor) within the same species or between different species.

As used herein, the term "consistency" or "consistent" is defined as the relative physical properties, including but not limited to matrix and density, of a corneal tissue, and particularly a corneal stromal matrix tissue, after sterilization and prior to opening, as compared to the matrix and density of the unprocessed native state of the same corneal tissue.

As used herein, the term "pliability" or "pliable" is also related to the relative physical properties of a tissue but is further specifically defined as the relative feel, elasticity, and strength of a corneal tissue, and particularly a corneal stromal matrix tissue, after sterilization and prior to opening, as compared to the feel, elasticity, and strength of the unprocessed native state of the same corneal tissue. The term "pliability" is referenced to determine, e.g., whether the tissue will sufficiently handle and hold sutures as well as a cornea in an unprocessed native state (a non-limiting example).

As used herein, the term "clarity" or "clear" is defined as the relative ability of a corneal tissue, and particularly a corneal stromal matrix tissue, after sterilization and prior to opening, to allow the same or nearly the same amount of light penetration, as compared to a corneal tissue in an unprocessed native state (i.e., the opposite of opaqueness, as generally defined).

As used herein, the term "submerge(d)," "submerse(d)," and/or "submersion" is defined as at least partially surrounded by a liquid or fluid (e.g., media). A "submersed" tissue thus may include both a tissue that is fully submersed and a tissue only partially submersed. Given the characteristics of the packaging discussed herein, it is possible for a tissue which is initially fully submersed in a media to move with relation to said packaging and/or media such that the tissue becomes only partially submersed (and vice versa, potentially an unlimited number of times). It is noted that such a transfer of state occurs because the packaging may be flexible, and the tissue also is flexible. Furthermore, it is noted that handling (e.g., by medical personnel) occurs without affecting the clarity, consistency, or pliability of the tissue within the packaging.

As used herein, the term "autograft" is defined as the use of the tissue within the same individual.

The use of the terms 'a,' 'an,' 'the,' and similar references in the context of this disclosure (especially in the context of the following claims) are to be construed to cover both the singular and the plural, unless otherwise indicated herein or clearly contradicted by context. Recitation of ranges of values are merely intended to serve as a shorthand method of referring individually to each separate value falling within the range, unless otherwise indicated, and each separate value is incorporated into the specification as if it were individually recited. All methods described herein can be performed in any suitable order unless otherwise indicated or otherwise clearly contradicted by context. The use of any and all examples, or exemplary language provided, is intended merely to illustrate better the invention and does not pose a limitation on the scope of the invention unless otherwise claimed. No language in the specification should be construed as indicating any non-claimed element as essential to the practice of the invention.

The present invention provides for a method to sterilize and preserve mammalian collagen tissue, in particular, human corneal tissue, from the time obtained until transplantation. The method generally comprises the following steps:

1. The corneal tissue arrives at processing facility in commercial storage media or with the whole eye globe in a moist chamber system.
2. The corneal tissue is evaluated and designated for long term preservation. Corneal tissue must meet clarity standards.
3. The corneal tissue is trimmed to remove excess tissue remaining from donor excision. Optionally, corneal tissue may be reduced to corneal stromal matrix with membranes, transected or further cut into various geometrically preferred shapes.
4. The corneal tissue is transferred to peel pouch container with absorbent material and media (rHSA) to achieve submersion of, e.g., from 1% to 99%. The media may or may not contain a cryoprotectant and clarity enhancer. The media may comprise other tissue protectants known in the art such as cryoprotectants, oxidation protectants, and protein denaturation protectants without limitations.

5. Optionally, the corneal tissue in preservation media is refrigerated or frozen and stored at −40 to −85 degrees Celsius prior to step 6 below to allow for batch processing.
6. The corneal tissue is shipped on wet ice to a sterilization facility in order to inhibit microbial growth before sterilization.
7. Electron beam irradiation of the corneal tissue occurs at ambient temperature (preferably within 2 days) after arrival as long as the tissue is maintained at refrigeration temperatures via refrigeration means or similar technology. Sterilization time can be 25 minutes or less, more preferably ranging from 2 minutes to 25 minutes, to complete once a sample is loaded onto the electron beam conveyor system. Sterilization time is defined as total time within the EBS vault. Preferably, the tissue is quickly removed from the refrigeration means and placed onto the conveyor belt while still cool. The cool starting temperatures and the short dwell time aid to reduce the temperature rise during the EBS process. Alternatively, and if irradiation is not achievable immediately, the tissue may be placed in refrigeration means until irradiated (this is preferable to placing the tissue on ice without refrigeration, if immediate irradiation is not achievable). During electron beam irradiation, the tissue receives 5, 10, 15, 20 or 25 kilogray (kGy) of electronic beam irradiation measured as a tissue internal dose by the methods well known to the skilled in the art. Using two electron beam accelerators opposite from each other and offset gives the shortest time for the irradiation to be completed, thus minimizing temperature increase. The alternative (if only one accelerator is used) is to have the conveyor system turn the container so that the other side may be irradiated—a process that takes additional time and can add to temperature rise.
8. Sterile corneal tissue is shipped back to the eye bank in an appropriate container without the need for ice or refrigeration means.
9. The corneal tissue is held in quarantine until safety is verified by Certificate of Irradiation based on dose mapping and validation. Cornea tissues are also subject to other quality assurance measures such as clarity and package integrity inspection.

The present invention overcomes the problems noted in the prior art by providing for a safer, more efficient and cost effective method to prepare and sterilize isolated mammalian collagen tissue, in particular, corneal tissue as well as other small-sized samples ("small-sized," as used throughout herein, is defined as having a width and/or length and/or diameter of 20 mm or less). The present method uses recombinant human serum albumin (rHSA) which is generated in cells from rice plants, and therefore does not contain pathogens present in normal human plasma. The present method uses partial submersion of the corneal tissue in the storage medium to make it easier to identify the tissue in the transparent peel pouch material, reduce the cost of production and to take advantage of a smaller, lighter, and break resistant packaging system. Partial submersion can be achieved with or without an absorbent material such as an hydroxylated polyvinyl acetal sponge (Fabco, New London, Conn.).

The present method uses electron beam as the source of sterilization, which may be performed at a temperature significantly (e.g., 50%) lower than that typically encountered for gamma irradiation, due primarily to the factors that (1) the electron beam generators are turned off before and after irradiation, and (2) a substantially shorter irradiation time (due to a higher dose rate) is required to achieve the same dosage as gamma beam irradiation. Both of these factors contribute to a lower cumulative temperature in the vault as compared to a gamma beam irradiation process, which, e.g., and in contrast to EBS, continuously heats such a vault. In addition, due to the way electron beams function and the way they are set up in radiation facilities, there is no need for costly and cumbersome dry ice protocols that can freeze the tissue and media which is customary when using gamma radiation in order to counter the temperature rise associated with gamma irradiation protocols and the elevated irradiation chamber temperatures. There is no need for other cooling means, without limitations (e.g., cold noble gas flow, Peltier cooling electronics, or operating in a cold room).

Another advantage of using electron beam to sterilize corneal tissue is the quantification of irradiation is more accurately and easily determined, making validations easier. Electron beam, by nature, does not penetrate as far as gamma radiation. Therefore, electron beam facilities are most often configured so that corneas can be irradiated in a simplistic linear array which virtually eliminated the three dimensional (3D) problems in establishing a uniform dose for all allografts in a lot/container. Gamma irradiation is usually performed in a three dimensional configuration which makes dose mapping much more challenging especially when dry ice is used as dry ice adversely affects many dosimeters and the weight of the dry ice is hard to consistently maintain from run to run. In particular, the uniformity of radiation absorption within the container is both hard to determine and regulate which can lead to inconsistent allograft properties or bioburden reductions (SAL's). When using electron beam it is much easier to achieve a uniform dose, thus achieving allograft consistency and sterility. In addition, the closed three-dimensional box traps heat generated internally during irradiation and may contribute to the heating issue described above.

The present method also may utilize peel pouch materials with a clear protective barrier, and/or aluminum oxide coated polyester-based films with superior gas and moisture barrier properties, rather than glass vials. Peel pouches result in less breakage and leakage and also stay clear during electron beam irradiation, which allows for better quality control, viewing capability, and safety in handling. In addition, peel pouches weigh less than glass which allows a reduction in shipping costs to and from sterilization facilities and distributors. Glass vials will also heat up faster and retain heat longer than peel pouches. Most importantly, the peel pouch comprising minimal media and a small-sized tissue is essentially a two-dimensional package and tissue system. This 2D system aids tremendously with the penetrating of the electron beam, thus keeping the dwell time of the process to a minimum, which in turn allows for (1) significantly shorter times in the vault, (2) controlling temperature rise, and (3) process consistency. The present invention thus provides for methods and systems comprising placing the tissue in a small package while simultaneously having a small volume of media. When combined with the feature that the packaged system is placed in front of the E-beam in a single file arrangement (i.e., a 2D arrangement), the following is achieved: (1) uniform and reproducible sterilization, that is, to achieve a SAL of $10^{-6}$ using the minimal dose possible, and (2) keeping the time in the vault under 25 minutes which in turn minimizes the generation of heat as well as aids in the dispersion/cooling of the tissue/package after e-beam sterilization.

Thus, it can be seen that the present invention provides for a beneficial and advantageous process that results in a safer, more consistent SAL, more efficient, and more cost-effective process for the preservation of isolated mammalian collagen tissue, in particular corneal tissue that provides consistent, pliable, and clear tissue that has been sterilized for extended shelf life. A pouch as described herein may further comprise a funnel shaped inner peal pouch of transparent film with an outer peal pouch. Such an embodiment is used primarily but not exclusively for smaller grafts or partial grafts (i.e. less than a whole/full-thickness corneal stromal matrix).

Alternatively, the present method may utilize Nalgene vials (Thermo Scientific, Waltham, Mass.) rather than glass vials. An outer peel pouch similarly surrounds the Nalgene vial. Nalgene vials will result in less breakage and stay clear after electron beam irradiation which allows for better quality control, customer viewing and safety in handling. In addition, Nalgene vials weigh less than glass which allows a reduction in shipping costs to and from sterilization facilities and distributors. Glass vials will also heat up faster and retain heat longer than Nalgene vials. Thus it can be seen that the present invention provides for a beneficial and advantageous process that results in a safer, more efficient and cost effective process for the preservation of isolated mammalian collagen tissue, in particular corneal tissue that provides consistent, pliable, and clear tissue that has been sterilized for extended shelf life. A Nalgene vial, as described herein, is used primarily but not exclusively for larger tissues, e.g., a whole, full-thickness corneal stromal matrix or larger-sized pieces of sclera ("larger-sized," as used throughout herein, is defined as having a width and/or length and/or diameter of greater than 20 mm).

It is further noted, with regard to the type of packaging and materials used therefor, the materials are chosen for their physical characteristics which include being able to withstand irradiation well and having a low oxygen transmission rate as well as a low water transmission rate. The low water transmission rate is particularly important as it helps prevent evaporation of the liquid inside (which is already a small amount by design), and it is a critical factor when it comes to having a long expiration date. Other choice materials could be, e.g., an aluminized layer on both sides of the package, as aluminum foil reduces O2 and H2O transmission even further. In the preferred embodiment, however, one side of the packaging is transparent so a surgeon can visualize the contents before opening the package. Any material that can replicate these functions, among others, could be chosen as the packaging material.

An embodiment provided by this disclosure is a tissue preservation media for use in the preparation of isolated mammalian collagen tissue. In some embodiments, the media is comprised of rice derived human serum albumin (15-25%) (Cellastim, Invitria, Ft. Collins, Colo.), rice derived human serum albumin (15-25%) and vitamin C (Sigma Aldrich, St. Louis, Mo.), rice derived human serum albumin (15-25%) and dimethyl sulfoxide (10%) (Sigma Aldrich, St. Louis, Mo.), rice derived human serum albumin (15-25%) with dimethylsulfoxide (10%) and vitamin C, rice derived human serum albumin (15-25%) and threhalose, or rice derived human serum albumin (15-25%) with threhalose and vitamin C. In other embodiments, the media is comprised of ovalbumin, ovalbumin and vitamin C, ovalbumin and dimethylsulfoxide (10%), ovalbumin with dimethylsulfoxide and vitamin C, ovalbumin and threhalose, or ovalbumin with threhalose and vitamin C. The dimethylsulfoxide exemplifies without any limitations a typical tissue protectant, in particular, a cryoprotectant. Vitamin C exemplifies without any limitations a radical scavenger.

The preferred embodiment of the present invention comprises a media comprising 20% rHSA and 80% sterile saline or liquid culture media. It was obtained experimentally that 20% rHSA is sufficient for optimal preservation of the tissue according to the present invention. Given the cost of recombinant albumin, it is optimal and cost-efficient to use the minimum sufficient amount of rHSA. Furthermore, and importantly, the concentration of albumin is also critical because the concentration controls the amount of water in the cornea. Too high a concentration of albumin causes water to leave the corneal tissue, resulting in thinning of the tissue, or worse, causing the tissue to lose its clarity. A concentration of albumin which is too low causes water to enter the tissue, making the tissue swell. Neither of these results is optimal and would make the tissue of inferior quality and/or unusable. The experimental data shows that 20% rHSA is the lowest concentration of rHSA that achieves the best results (i.e., the most identical result to natural tissue, including consistency, pliability, and clarity). Although higher concentrations of rHSA may be used, it would be more expensive and could further affect the tissue as noted above. Additionally, concentrations of rHSA above 50% are difficult to achieve due to its solubility at the physiologic conditions required for storage and transplant. For experimental evidence, see FIGS. 3-8.

Figure 2:
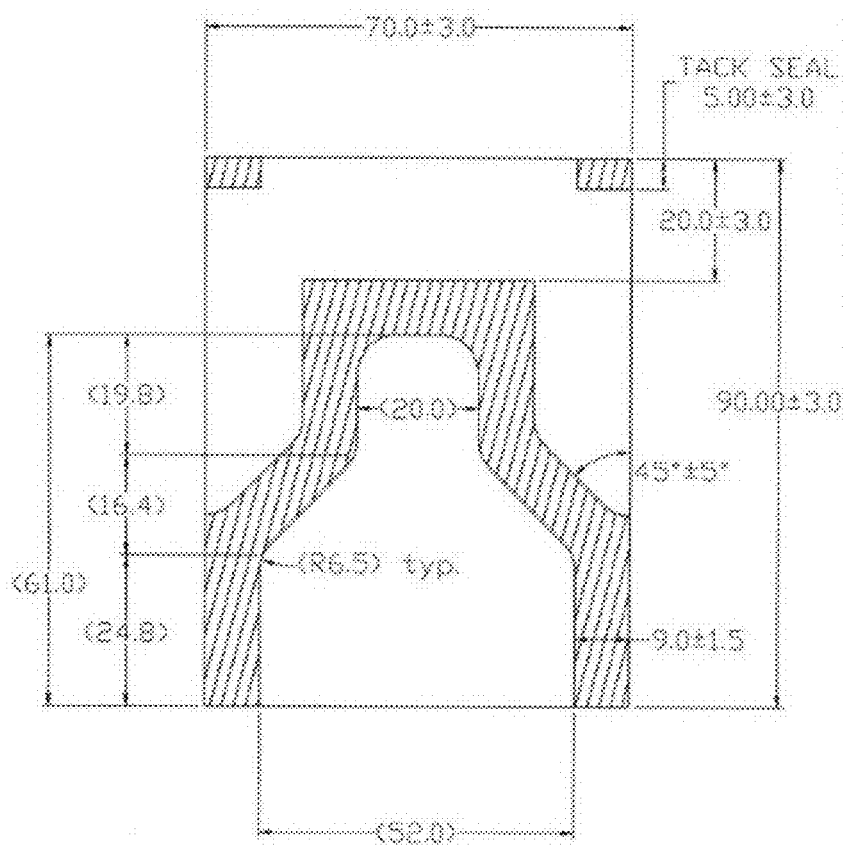
FIG. 2 shows an exemplary embodiment of a pouch for packaging of tissue for sterilization and storage, according to the present invention. It is noted that the exemplary packaging shown in this Figure is positioned upside-down (i.e., the top/opening of the package is located at the bottom of the Figure). The pouch is heat sealed after adding rHSA and tissue. The opening/reservoir of the example pouch has a maximum width of 52 mm and a minimum width of 20 mm (the minimum width area is the preferred area for placement of the tissue and the media discussed herein). Such a maximum/minimum relationship defines the dimensions of the funnel-shaped reservoir of such packaging, as discussed hereinbelow.
Figure 3:
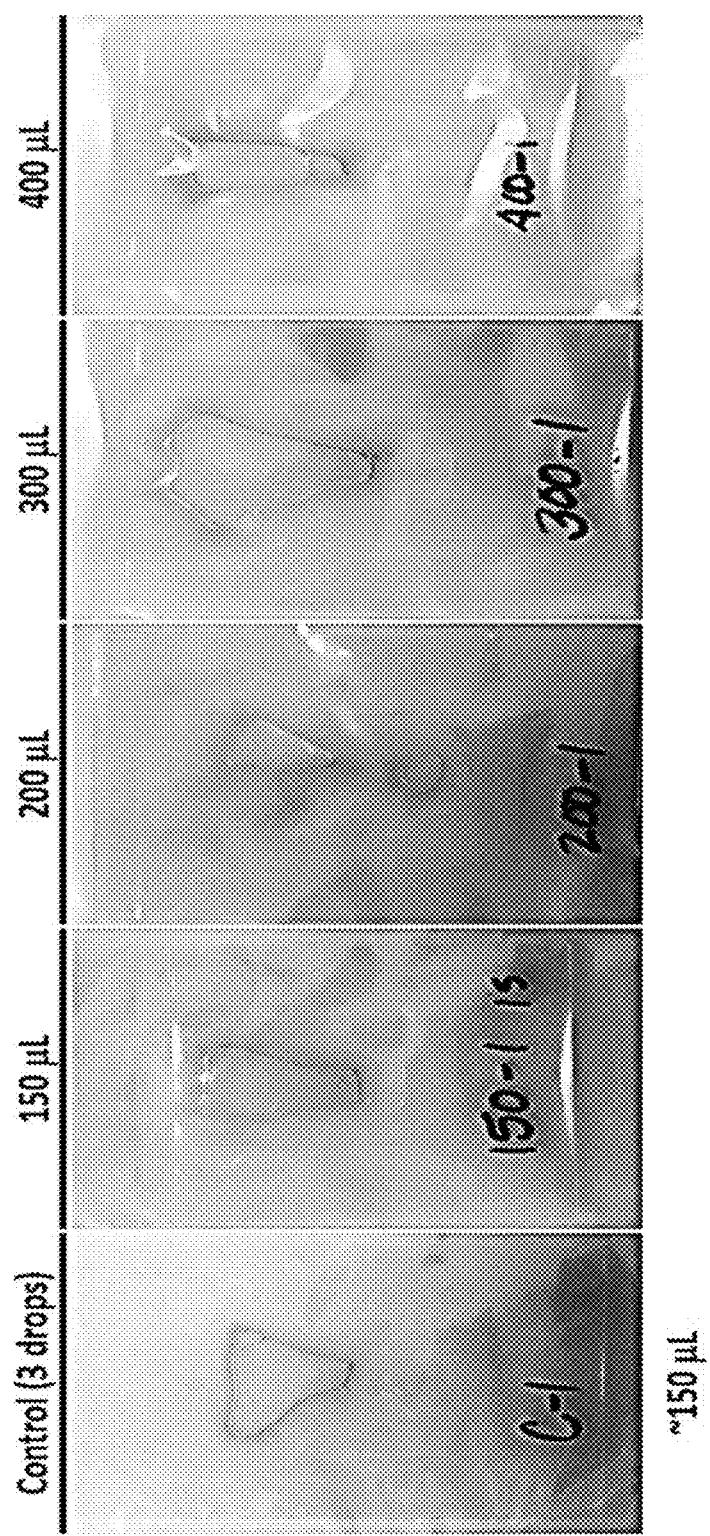
FIG. 3 shows experimental results from an exemplary study. These experimental results illustrate the threshold amount of rHSA necessary to carry out the present invention (i.e. approximately 300 microliters). Less than 300 microliters may result in drying out of the corneal tissue, thus about 300 microliters or more is preferred.
Figure 5:
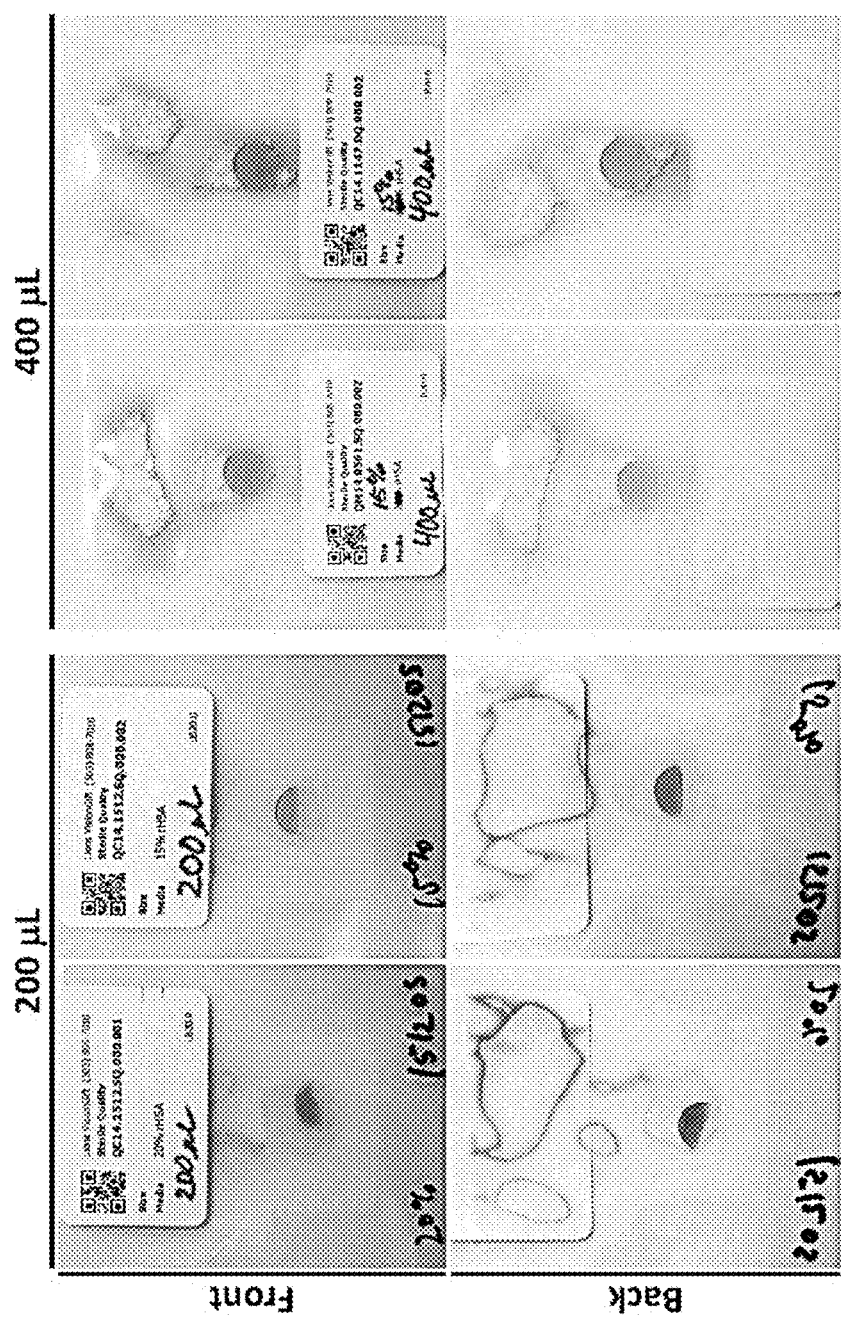
FIG. 5 shows results of a study comparing tissue samples, processed, packaged, sterilized, and stored according to the present invention, which have been placed in either 200 or 400 microliters of rHSA. After accelerated aging, the results show that 300 and 400 microliters show comparable results in that they did not dry out. The samples containing 200 microliters of rHSA, however, are substantially dryer than those with approximately 300 microliters or more, and thus less compatible (perhaps incompatible) for the disclosed process.
Figure 6A:
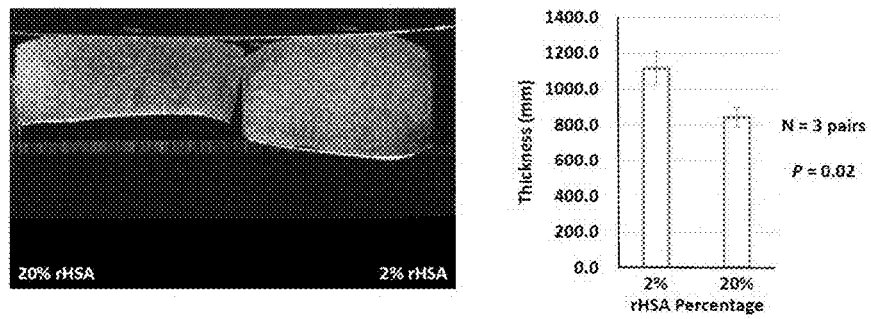
FIG. 6A shows summary (n=3) experimental results for the effect of a specific amount of rHSA (2% rHSA vs. 20% rHSA) on tissue thickness (i.e. consistency). The results show that 20% rHSA reduces the thickness of halo corneas by about 24.4%, as compared to 2% rHSA. Thinner is better.
Figure 6B:
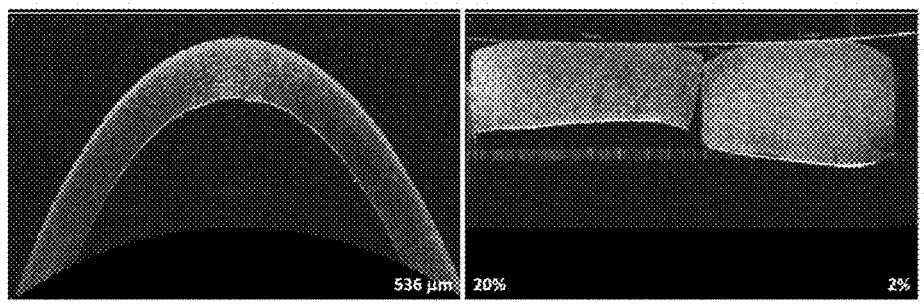
FIG. 6B shows experimental results illustrating before-EBS (Electron Beam Sterilization) and after-EBS comparison images of the same tissue, wherein a first tissue is stored in 2% rHSA and a second tissue is stored in 20% rHSA. The results show that the original thickness prior to processing was 536 μm, and corneal thickness after processing was 780-807 μm (20% rHSA) and 909-1,220 μm (2% rHSA). The 20% concentration keeps the corneal tissue thickness closer to normal.
Figure 6C:
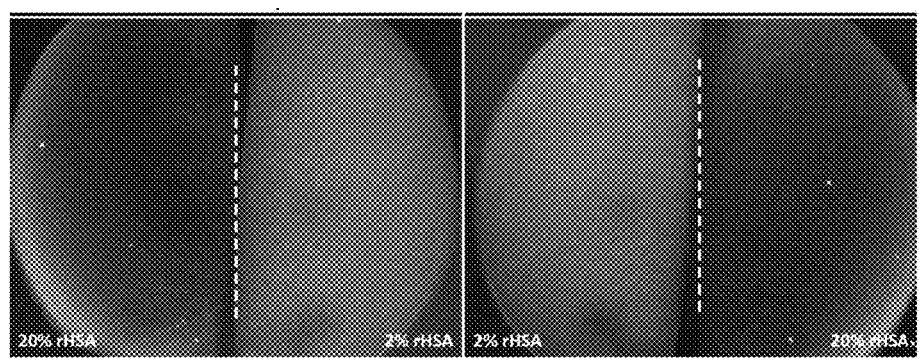
FIG. 6C shows an experimental comparison illustrating clarity differences between tissues stored in 2% rHSA and fs stored in 20% rHSA. The results show that a storage media comprising 20% rHSA provides a clearer tissue than a storage media comprising 2% rHSA.
Figure 7A:
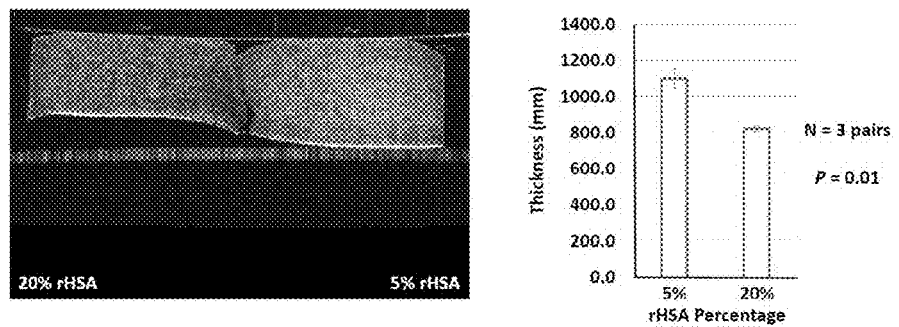
FIG. 7A shows summary experimental results for the effect of a specific amount of rHSA (5% rHSA vs. 20% rHSA) on tissue thickness (i.e. consistency). The results show that 20% rHSA reduces the thickness of halo corneas by about 25.2%, as compared to 5% rHSA.
Figure 7B:
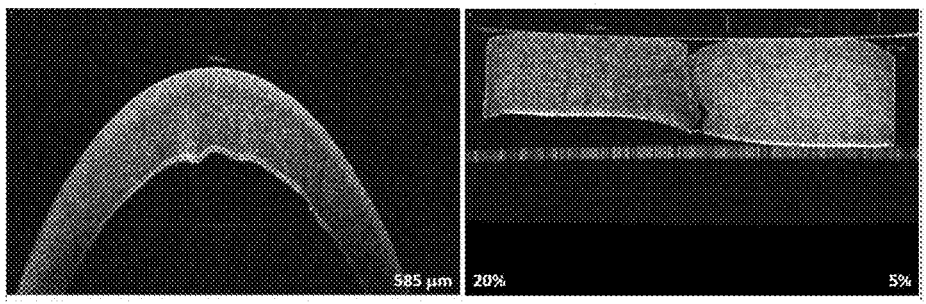
FIG. 7B shows experimental results illustrating before-EBS and after-EBS comparison images of the same tissue, wherein a first tissue is stored in 5% rHSA and a second tissue is stored in 20% rHSA. The results show that the original thickness prior to processing was 585 μm, and corneal thickness after processing was 796-813 μm (20% rHSA) and 907-1,070 μm (5% rHSA).
Figure 7C:
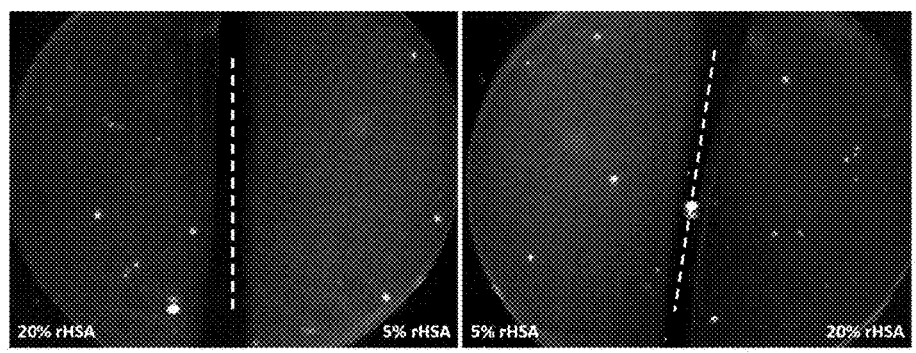
FIG. 7C shows an experimental comparison illustrating clarity differences between tissues stored in 5% rHSA and tissues stored in 20% rHSA. The results show that a storage media comprising 20% rHSA provides a clearer tissue than a storage media comprising 5% rHSA.
Figure 8A:
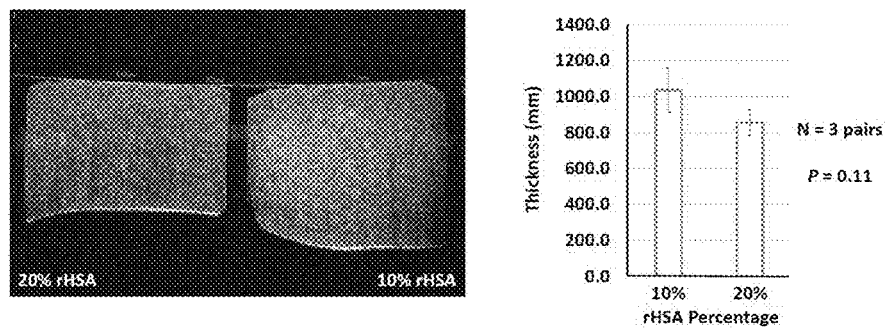
FIG. 8A shows summary experimental results for the effect of a specific amount of rHSA (10% rHSA vs. 20% rHSA) on tissue thickness (i.e. consistency). The results show that 20% rHSA reduces the thickness of halo corneas by about 17.5%, as compared to 10% rHSA.
Figure 8B:
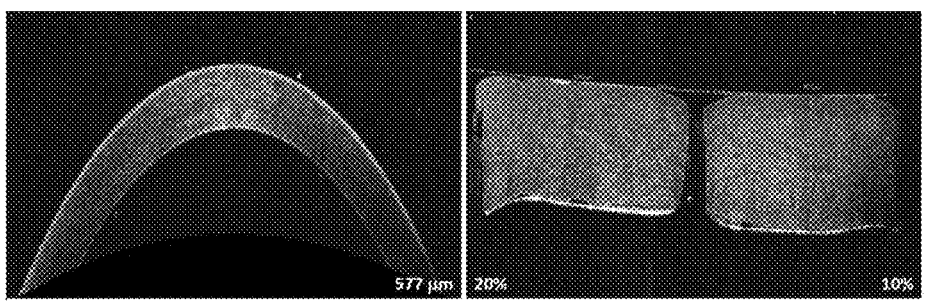
FIG. 8B shows experimental results illustrating before-EBS and after-EBS comparison images of the same tissue, wherein a first tissue is stored in 10% rHSA and a second tissue is stored in 20% rHSA. The results show that the original thickness prior to processing was 577 μm, and corneal thickness after processing was 846-883 μm (20% rHSA) and 914-982 μm (10% rHSA).
Figure 8C:
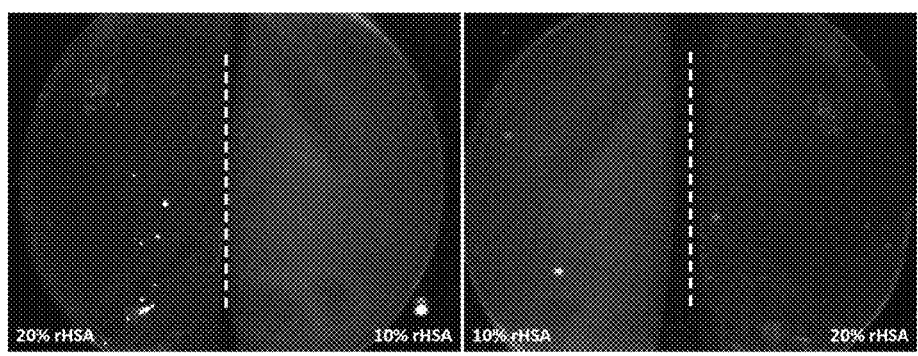
FIG. 8C shows an experimental comparison illustrating clarity differences between tissues stored in 10% rHSA and tissues stored in 20% rHSA. The results show that a storage media comprising 20% rHSA provides a clearer tissue than a storage media comprising 10% rHSA. Note; We did not test concentrations of rHSA above 20% as our purpose was to use the minimum amount of rHSA needed to achieve clear corneas of clinically appropriate thickness for transplant. Although, concentrations of rHSA up to approximately 30% could well provide useful corneas, this would add significant and needless cost to each tissue. Additionally, the darker color of the increased concentration of rHSA adds an esthetically unacceptable level of yellowing to the tissue.
Figure 9A:
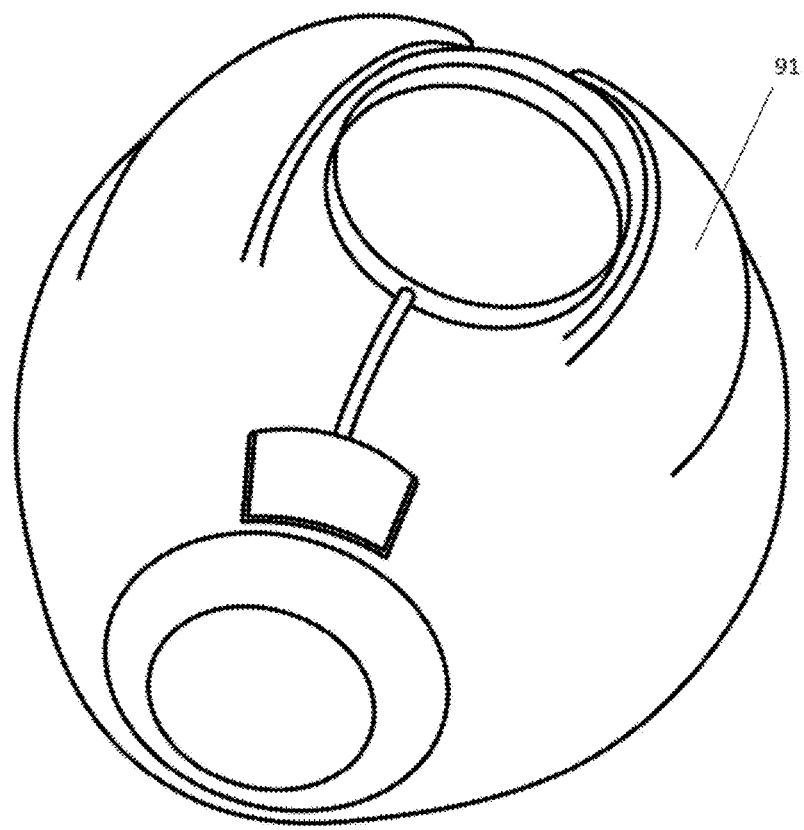
FIGS. 9A-9G show example illustrations of the various examples of the types of grafts which can be formed from a single cornea or a plurality of single corneas. Each Figure is further described hereinbelow.
Figure 9B:
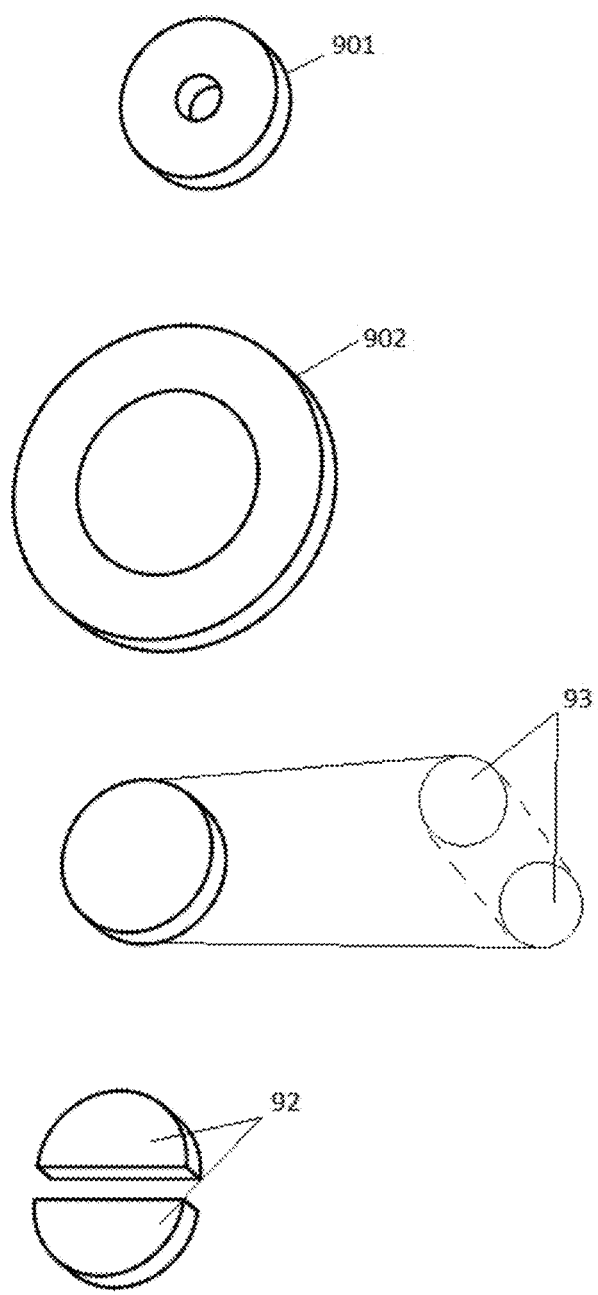
Figure 9C:
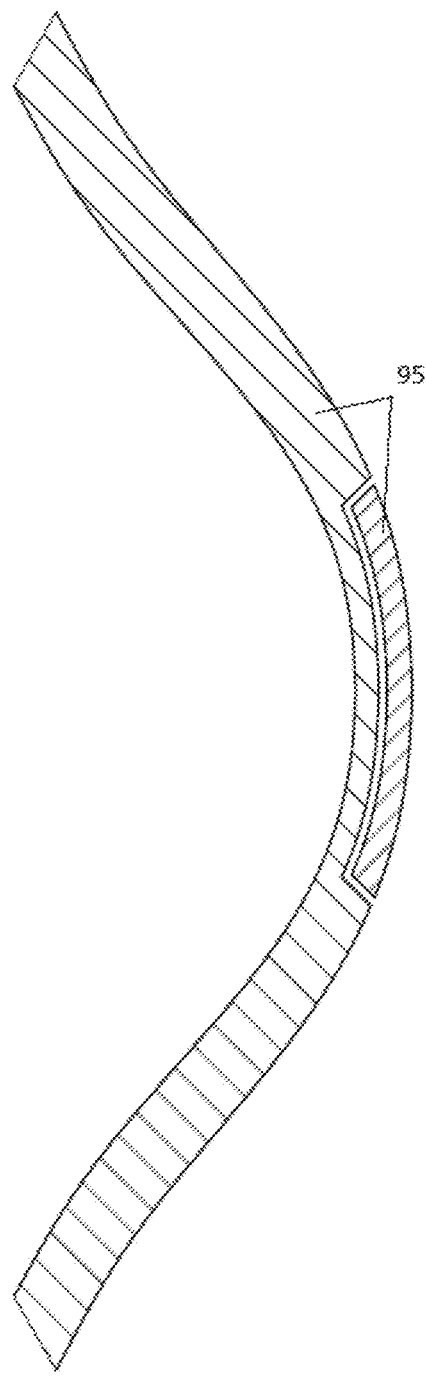
Figure 9D:
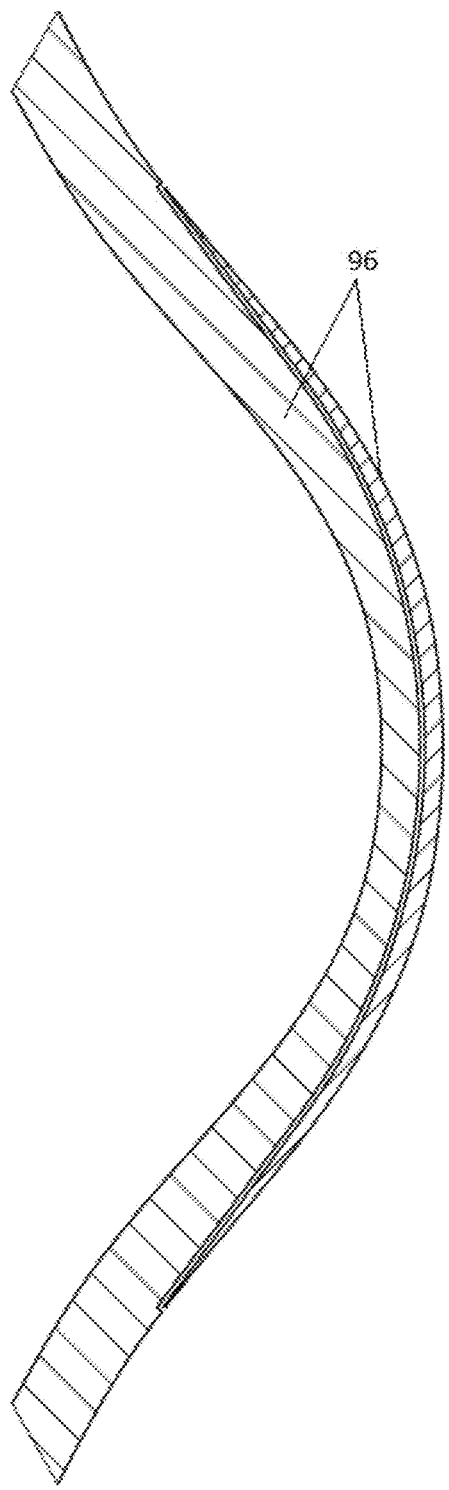
Figure 9E:
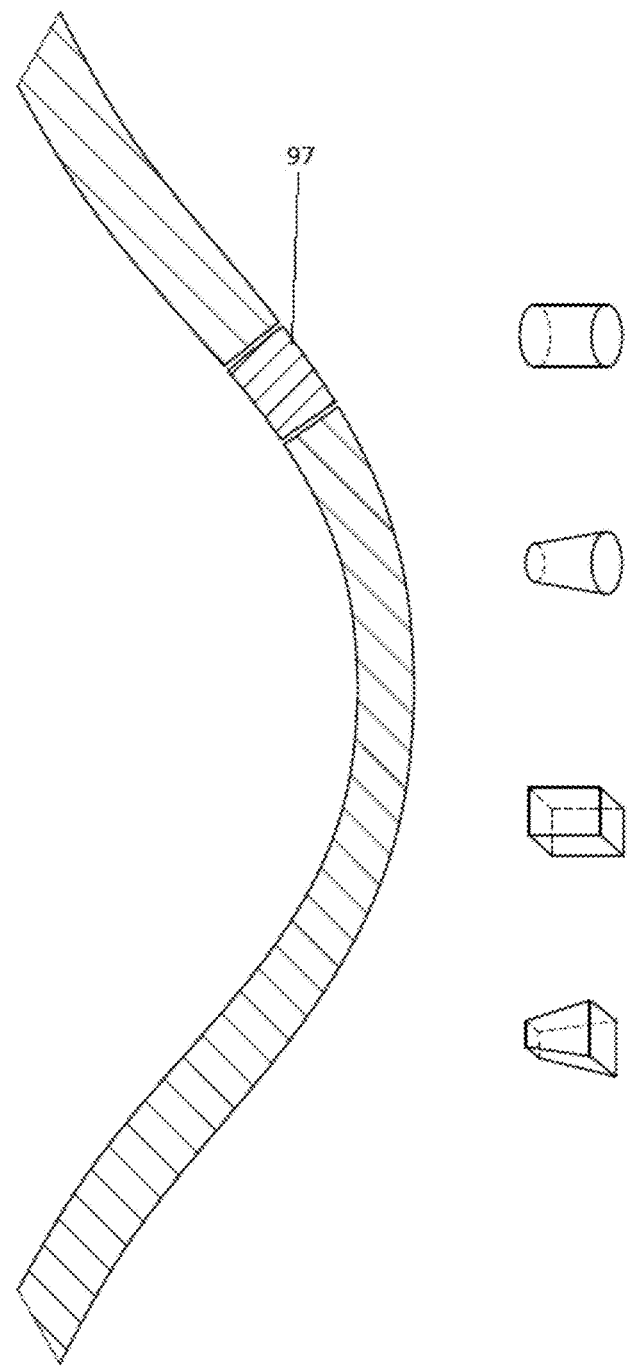
Figure 9F:
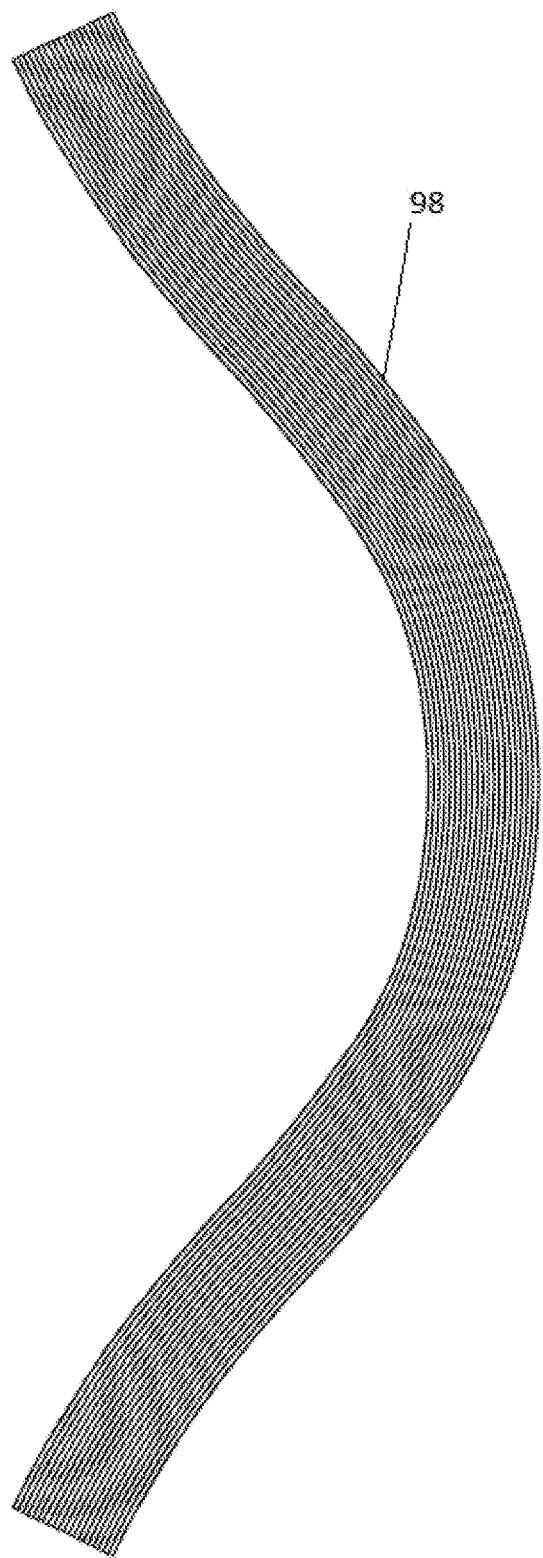
Figure 9G:
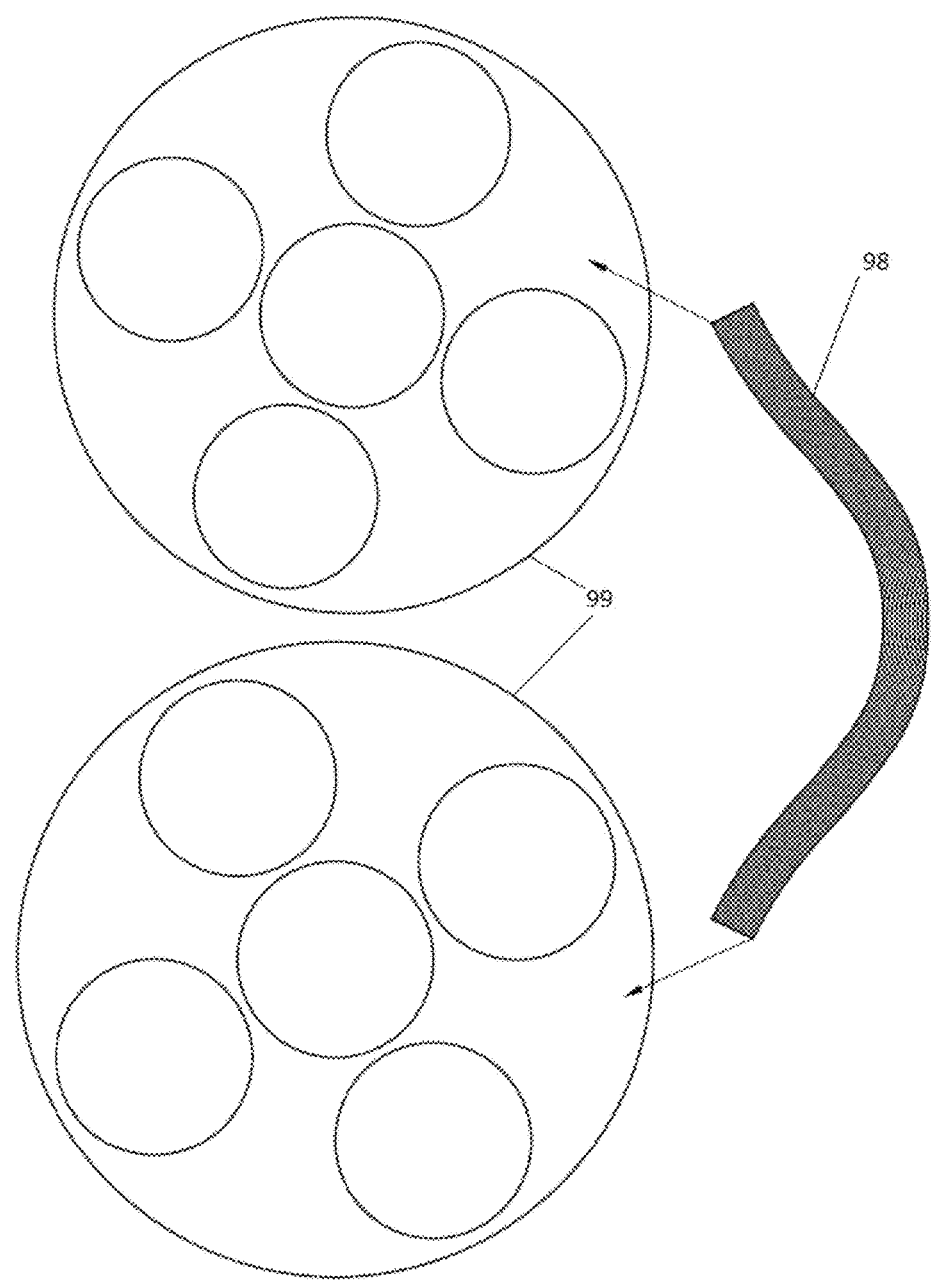

The following embodiments disclose exemplary variations of the step of partially submerging isolated mammalian collagen tissue to maintain tissue hydration and for other storage purposes. In one embodiment, a storage container (FIG. 2) is filled with an amount of tissue preservation media to only partially cover the mammalian collagen tissue. In another embodiment, an absorbent material, such as a hydroxylated polyvinyl acetal sponge (PAV c, Fabco, New London, Conn.) or cellulose sponge, is introduced into a peel pouch with tissue preservation media which does not fully submerge the mammalian collagen tissue. The absorbent material may be pre-soaked in tissue media or may serve as a dispersion method for keeping the collagen tissue both preserved, hydrated and separate from the tissue media already present in a sealed/air tight pouch or act as a support either alone or in combination with another material which helps maintain the natural curvature of the corneal tissue. The pouch material is a combination of clear protective barrier films which are aluminum oxide coated polyester-based films with superior gas and moisture barrier properties similar to that of foil. Alternatively, one side of the pouch and/or second pouch may be comprised of a foil layer to decrease the gas and water vapor transmission rates on one side of the pouch while maintaining the ability to easily view the tissue through the other clear side of the pouch. It follows that if the outer and inner pouches both comprise such an embodiment (i.e., one foil side, one clear side), the inner and out pouches' sides must line up for viewing purposes. The material is flexible and strong and has excellent puncture resistance. The pouch provides good clarity for cornea visibility and is radiation sterilizable. The unique size and design of the pouch is ideal for using a minimum amount of media (as little as approximately 0.3 ml, or 300 μl) for the preservation of the corneal tissue. The size of the inner pouch may be sized larger to accept other tissues that may require more space or media. The attributes of the packaging system would remain, albeit with slightly more mass and cost. This design keeps the cost of the resulting transplant packaging system very cost effective. The total size of the final packaging system which weighs approximately six (6)

grams (both peel pouches, label, media and tissue) also aids in reducing the cost of shipping. The pouch is heat sealable after the cornea and media are added and can be placed in a second over pouch which is also heat sealable to maintain the sterility of the inner pouch and to make the packaging system even more robust as well as safer to handle aseptically in the operating theater. The most advantageous feature of the package is the great ease of locating the hard to visualize tissue in the media as compared to other available packaging systems such as glass that turn brown when irradiated and contain much more media which makes the identification and removal of the clear corneal tissue difficult. The seal is peal-able to facilitate easy opening and removal of the corneal tissue with a sterile instrument using standard operating room aseptic technique.

Furthermore, the packaging materials discussed above optimize the following: (1) resistance to the irradiation process, (2) maintaining water transmission (i.e., evaporation) at a minimum level (if water evaporates, the tissue becomes unusable and/or has a shorter shelf life), (3) opening of the seal after irradiation (it is noted that prior art seal materials do not open easily, if at all, after irradiation), and (4) protecting the tissue from contamination. Regarding the size and shape of the packaging, the package is designed to be the smallest possible but which is still able to hold the tissue combined with the minimum amount of rHSA required to maintain the tissue for at least two years after irradiation. The package is designed to make the processing of the tissue easy and practical (i.e., when the tissue and rHSA are placed into the package, it is easily performed). The difficulty in packaging these together in any smaller of a package than that disclosed results in distressed tissue, spills, and other accidents.

One example embodiment that would increase the shelf life based on packaging design would be to use foil on both sides of the outer and/or inner packaging. The foil slows down the evaporation rate and thus increases the shelf life. The disadvantage, however, would be that a doctor could not visualize the tissue before opening the packaging. Such a design decision would be made based on the weighing of factors including but not limited to whether the extended shelf life outweighs the risk of a doctor not visualizing the tissue prior to opening.

In another embodiment Nalgene vials topped with irradiation resistant stopper and peelable crimps within outer peel pouches (Chevron pouch, Oliver-Tolas Healthcare Packaging, Feasterville, Pa.) were used prior to sterilization.

An embodiment provided by this disclosure is a method for preparing isolatedmammalian collagen tissue for transplantation. In one embodiment, mammalian collagen tissue is initially placed in storage media, preferably Optisol GS (Bausch & Lomb, Costa Mesa, Calif.) and evaluated for long term preservation. The mammalian collagen tissue is subsequently processed and placed in tissue preservation media, shipped to a sterilization facility on wet ice, sterilized at ambient temperature, and then return shipped to an eye bank. In one embodiment of the present method, the mammalian collagen tissue is corneal tissue. Preferably, the corneal tissue lacks an endothelial layer. More preferably, the corneal tissue has been trimmed (Lions VisionGift, Portland, Oreg.). Trimming can include transection of the corneal tissue. Preferably, the corneal tissue has been trimmed such that it comprises the corneal stromal layer.

An embodiment provided by this disclosure is a method for sterilization of mammalian collagen tissue for transplantation. In one embodiment, the mammalian collagen tissue is exposed to electron beam irradiation (NUTEK Corporation, Hayward, Calif.). Preferably, the electron beam provides 10 MeV (10 million electron-volts) of energy. In another embodiment, the electron beam source is best made up of two different beams coming from opposite sides and offset (i.e. the beams are not aimed directly at each other). Preferably, the two different beams would be offset at the minimum space technically feasible to achieve the shortest time in the beam field and the vault, and to minimize the exposure to elevated temperatures. Collagen exposure to electron beam irradiation may last up to 25 minutes (using a 10 MeV, 8 Kw system) but is only necessary for as long as necessary to achieve sterilization of the particular tissue (s). It is noted that using a 10 MeV, 20 Kw system, for example, may further reduce the time required in the vault, as the conveyer belt would move 2.5 times faster. In another embodiment, collagen tissue is put on wet ice or another temperature reducing material like reusable "ice blocks" to keep collagen from warming to ambient temperature during electron beam irradiation. Since, the linear arrangement of tissue (single file) is preferred, the cooling blocks, ice or equivalent is positioned either above or below or both so the cooling materials do not fall in line between the e-beam and the tissue. This practice is advantageous, e.g., in areas where environmental temperatures are elevated or vault times are extended.

An embodiment provided by this disclosure is a method for storing mammalian collagen tissue for transplantation. In one embodiment, collagen tissue is placed into an inner, biocompatible, clear plastic peel pouch of specific design (see FIG. 2) with such inner peel pouches containing collagen tissue placed in second, bio-compatible, outer peel pouches (Chevron pouch, Oliver-Tolas Healthcare Packaging, Feasterville, Pa.) prior to sterilization. The sterilization is facilitated by placing the tissue in the center of the inner pouch due to a special design serving this purpose, the design is without limitations.

Another embodiment provided by this disclosure is a method for storing mammalian collagen tissue for transplantation. In one embodiment, collagen tissue is placed into Nalgene vials (Thermo Scientific, Waltham, Mass.) used with stoppers and crimp seals made of aluminum or plastic, or both, before sterilization. In other embodiments, external packaging (i.e. a second, outer pouch or other packaging) can be provided for the pouch transportation, to ensure that the inner pouch arrives in the operating room in the condition compatible with high sterility/aseptic procedures inherent to the surgery environment. In yet another embodiment, collagen tissue is placed into Nalgene vials topped with aluminum or plastic, or both, and placed in medically compatible peel pouches (Chevron pouch, Oliver-Tolas Healthcare Packaging, Feasterville, Pa.) prior to sterilization.

Features of an EBS (Electron Beam Sterilized) sterile cornea, sources and benefits to eye banks. An objective of the present invention is to provide a sterile, clear cornea for tectonic applications. However, two other major advantages are also to be gained, each of which is as important as sterility. Because endothelial cells preservation is not a priority and sterility is achieved, the cornea does not need to be refrigerated after sterilization in rHSA, and in theory, sterility can be maintained indefinitely assuming the package integrity is maintained. On a practical basis, such sterilization provides for an expiration date of 2-5 years from the time of sterilization. Additionally, the absence of viable cells within the container negates the need for refrigeration. Therefore, EBS corneas may be kept at ambient/room temperatures. This is an improvement over the current technology's requirements for storage of corneal tissue of 14 days and near freezing refrigeration at around 2-6 degrees Celsius.

Sterility. Corneas provided by eye banks have a strong safety record but every year there are reports of bacterial and fungal infections that are attributed to the donor cornea. Although small, this is an unavoidable risk when providing tissue for endothelial grafting. For tectonic grafting this risk can now be eliminated. Sterility is also enhanced by placing each cornea into a sealed, double peel pouch system prior to sterilization, thus insuring that the contents are sterilized in a closed system, the closed system remaining sterile until opened. This seal can then be validated to ensure that it is dependable until opened. In comparison, a cornea which is placed into a commercially purchased vial with media (the vial must be opened for such placement) and then recapped using the same cap is, by definition, is no longer a validated seal. Therefore, everything inside the commercially purchased vial is not sterile. Furthermore, the outside of such a commercially purchased vial is neither sterilized nor subsequently placed in an outer package/barrier to further protect the commercially purchased vial. Therefore, the outside of commercially purchased vials is also not sterile and not protected by a barrier. In contrast, everything inside the outer peel pouch of the present invention is sterile. Unlike traditional corneas provided in a cold storage packaging, and utilizing the method and system described herein, the Operating Room staff does not have to compromise their sterile field when introducing the cornea into the operating theatre.

Viral Disease. The risk of viral disease transmission for endothelial corneal transplants is less than the risk for bacterial infections. Yet the risk of viral disease transmission can now also be nearly eliminated for tectonic applications. While Bovine Spongiform Encephalopathy (BSE) is not a virus, it should be noted that while irradiation is thought to reduce the risk for transmission of BSE, there is no evidence that this new corneal processing method fully eliminates this risk. This stems from the fact that BSE may exist in the tissue itself, since it cannot come from the rHSA media. Thus, the theoretical risk of BSE transmission, albeit quite low, must remain. This risk is further minimized via irradiation as described herein.

Refrigeration. Unlike the need to keep corneas in cold storage media refrigerated between 2-6° C., after irradiation, the EBS cornea can be kept at ambient, room temperature. Exposure to extreme high temperatures and freezing temperatures should still be avoided. This provides obvious advantages for the eye bank but also for hospitals and surgery centers storage prior to surgery.

Shelf Life. Cold storage media's stated storage limit is 14 days according to the manufacturer. On a practical basis, corneas in the United States are rarely used beyond 7 day storage. Extending storage from 14 days to two years or longer is a monumental improvement. It would also allow surgeons/hospitals with a large patient census to store sterile corneas at the hospital for emergency cases such as perforations of the surface of the eye.

Cornea Processing. Terminal sterilization (as commonly understood in the art, e.g., according to ANSI/AAMI ST67:2011) allows for corneas to be further processed before sterilization by the tissue bank into allografts of certain shapes, sizes, and thicknesses that would be problematic otherwise due to the increased probability of contamination. One very desirable example is the split thickness sterile cornea.

Cornea Supply. The EBS Cornea processing technology allows an eye bank to expand their surgical cornea supply in two ways: Grafts previously considered unsuitable for surgery (e.g. corneas with a low endothelial cell count) can be designated for sterile cornea processing if there is a clear, intact corneal stroma. Within the United States eye banks, 75 of every 100 donor corneas are provided for surgical use. We estimate that an additional 10% of these corneas can be provided as a sterile cornea increasing the surgical cornea percentage to 85%. Eye banks starting with a lower surgical percentage stand to realize greater improvements. For decades, eye banks operated under the premise that one donor may yield a maximum of 2 corneal grafts. The EBS cornea will allow for splitting one cornea into four (4) grafts with split thickness, half-moon grafts, popularly used in glaucoma surgery to secure the tubes with certain glaucoma shunt/valve designs. Surgical Application: The EBS Cornea will be distributed for certain tectonic (non-endothelial) applications.

As noted above, one advantage of the present invention is that tissue may now be split and partial corneas can be stored to increase the supply of transplantable tissue from eye banks. Although it has always been possible to split or cut a cornea into any shape or size, it was never logistically feasible, and therefore not commercially viable or surgeon friendly. The limiting factors have been storage time, clarity, pliability, and/or consistency of the cornea itself. The present invention combines long term preservation of a clear corneal stroma stored at room temperature, thus allowing for multiple grafts of the same cornea to become commercially viable without being limited by the factors of storage time, sterility, clarity, or consistency. Such practicality and commercial viability of cutting a cornea into 4 or more pieces has not previously been achieved.

Types of grafts achievable by the method of the present invention comprise the following non-limiting examples (see FIGS. 9A-9G):

1. 1 graft—an intact full thickness stromal graft 94. In another exemplary embodiment, the cornea may be pre-cut with center aperture 901, e.g., to enable use with a keratoprosthesis implant. In another exemplary embodiment, a cornea may be a full thickness cornea (clear center) with a scleral rim (white portion of the eye) 902 for surgeons who prefer to cut their own graft (this provides a flexibility on diameter for tectonic (structural) and surface grafting.
2. 2 half grafts—cutting a cornea in half resulting in two half-moon-shaped full thickness grafts 92 (e.g., glaucoma tube valve application).
3. 2 split grafts—making a transactional cut through a cornea resulting in two split thickness grafts of equal shape 93 or otherwise desired 95, 96 length or shape (e.g., corneal overlay).
4. 4 grafts—combining the 2 previous cuts (2, 3) resulting in four half-moon-shaped, split thickness grafts (not shown in figures, but a combination of 92 and 93) (e.g., glaucoma tube valve application).
5. 10-12 grafts 97—circular or square, smaller diameter or width, full thickness punches or a full thickness cornea (e.g., patch grafts, corneal inlay).
6. 20-24 grafts—using (5) above, and doubling the number of grafts by using split thickness punches or a split thickness cornea (e.g., patch grafts).
7. 20 grafts 98—micro thin lamellae cuts having a thickness of 15 to 20 microns (e.g., corneal overlay, corneal inlay).
8. 100 grafts 99—circular cuts of micro thin lamellae (each lamella having a 15-20 micron thickness), each circular cut having a diameter of approximately 3 mm or less (e.g., corneal inlay). It is noted that the lamellae are cut from the top-side or the bottom-side, similar to the direction of the punch in FIG. 9G. Thus, the splitting of the lamellae of a single tissue occurs along a first plane, while the circular cutting of the micro thin lamellae occurs on a plane perpendicular (or at least substantially perpendicular) to the first plane.

Glaucoma Tube Valves. Many surgeons are using cornea to secure and protect the tube for implants such as the Ahmed Valve and the Baerveldt Glaucoma Implant. The EBS cornea's clarity and thickness provides a clear window of the surgical site for the surgeon as well as an aesthetically pleasing cosmetic look for the patients Patch Grafts. The sterile cornea will be used in corneal patch grafts (in full thickness or split thickness) often to treat surface ulcers or very thin corneas.

Emergency Corneas. It is not unusual for a busy corneal surgeon, department of ophthalmology or eye center to be presented with patients needing grafting immediately. A corneal perforation, for example, can be treated immediately if the eye center keeps a sterile cornea(s) in stock at the eye center rather than risk this occurring on a day the eye bank may not have an available cornea or deliver in timely fashion which can cause undo stress to both the patient and surgeon.

The flow-chart in FIG. 1 provides the summary of the technology.

1. A corneal tissue or enucleated eye is excised from a donor 101.
2. The corneal tissue, packed in wet ice, arrives at a processing facility 102, being transported in a commercial storage media (i.e. organ culture based media) or intact as a whole eye globe in a moist chamber system 103. If the cornea was excised in situ, the cornea is placed and transported in a commercial storage media (e.g., Optisol GS) until it is received by the eye bank laboratory prior to tissue evaluation. In the case of an enucleated eye, it is placed in ice cooled, moist chambers until it is received by the eye bank.
3. Enucleated eyes are evaluated, the corneas from acceptable (i.e. meeting standards) enucleated eyes are excised in the eye bank laboratory, and those corneas excised are placed in an organ culture media (e.g., Optisol GS) and returned to refrigeration. At this step in the process and prior to evaluation of the corneal tissue itself, such organ culture media is required because the application of the particular tissue has yet to be determined. For many applications, such as posterior endothelial transplants, the cells within the tissue must be both high in number and viable. Such applications are given priority over others. The organ culture media increases the chances that more cells remain viable, and not using such preservation media renders the tissue useless for such applications. In contrast, the present method requires no viable cells and may make use of a tissue that is useful yet not fit for applications requiring viable cells.
4. Continuing the process of the present invention, the corneal tissue is further evaluated for applications of the present invention and must be designated for long term preservation, i.e., the corneal tissue must meet specific clarity standards 104. It is noted that such standards are based on clarity standards known to those skilled in the art; however, the process disclosed herein requires significantly less of the clear tissue to be intact and packaged.
5. The designated corneal tissue is trimmed to remove excess tissue remaining from the donor excision. In some embodiments, the tissue is frozen and then trimmed. The trimmed (or untrimmed) tissues may be stored at a lower temperature (e.g., −40 degrees Celsius or below until enough tissues are amassed to create a sufficient batch for e-beam sterilization. Although such storage at a lower temperature is not required to carry out the present invention, it may be preferable to sterilize tissue in large batches in order to achieve lower per-allograft-unit costs associated with EBS and EBS facilities. If such a storage step is included in the process, and once a sufficient amount of tissue has been amassed, the corneal tissue may further be (1) reduced to a corneal stromal matrix with membranes, (2) transected, (3) cut into various geometrically preferred shapes 105, or (4) used whole. Preferably, the tissue is at least trimmed and reduced to a corneal stromal matrix with membranes. Furthermore, the tissue is preferably cut/divided and/or trimmed prior to packaging, then frozen (if necessary) in order to achieve a large batch size, then thawed (if necessary), and then sterilized. The reduction, transection, cut, or other division of the tissue may be performed, e.g., with a scalpel, a blade, an instrument such as a microkeratome, or a tool such as a femtosecond laser. In addition, a stainless steel punch or a trephine punch may be utilized to punch a central cornea aperture, to punch the outer rim of the cornea, or to punch patch grafts.
6. As noted above, the corneal tissue in the preservation media may be refrigerated or frozen and stored at −40 degrees Celsius or below (normally between −40 and −85 degrees Celsius), should long term preservation be required prior to irradiation. After irradiation, no refrigeration or freezing is required whatsoever. In some embodiments, corneal stromal grafts processed using the disclosed method are cut after they are initially processed and frozen, being cut to a desired shape and size based on application. In other embodiments, processed tissue is frozen and then cut. Such storing at lower than ambient temperatures is performed to make the process more commercially feasible because it is more cost effective to e-beam sterilize large batches of prepared corneas at one time. For example, 250 to 350 corneal grafts may be sterilized at one time using e-beam sterilization according to the present invention. In other embodiments, up to thousands of grafts may be sterilized at once. Increasing the number of grafts that are sterilized at one time reduces the per allograft cost of sterilization, as some costs are fixed. Thus, freezing at some point(s) prior to sterilization, although not required by the presently disclosed method, makes the present invention scalable for any sized operation or any need, including but not limited to emergency situations.
7. If not already performed, the corneal tissue may then be transferred to a custom container (i.e. vial, packaging) 106, as disclosed herein. In the preferred embodiment, the corneal tissue, after initial processing, is packaged prior to any freezing which occurs prior to sterilization. If frozen according to the step directly above and without packaging, the tissue is first thawed, then batched/cut, and finally placed in the custom container of the present invention.
8. The corneal tissue is immersed in a tissue preservation media comprised of recombinant human serum albumin (rHSA). Even partial immersion in rHSA is sufficient, which is an unexpected result. Optionally, however, an additional absorbent material may also be placed within the container to achieve a partial submersion of the tissue, from 1% to 99% submersion, based on the size and condition of the tissue. The partial submersion may be conducted in a range between about 1% and about 10%, and between about 10% and about 99%. This feature of partial submersion (cf., full submersion) leading to desired results (i.e. clarity, pliability, consistency) was, during experimentation, an unexpected result, as one skilled in the art would expect the tissue to dry out, at least partially, if full submersion is not achieved or if no additional absorbent material is used (See FIGS. 3-8 for exemplary evidence of experimental results). Based on this discovery, it was found that partial submersion in rHSA alone (i.e. without any absorbent material and without full submersion) is sufficient for achieving desired results according to the present invention. This fact leads to several advantages: (1) no vial-like inner container is required, (2) a remarkably smaller amount of rHSA is required per package (the range of effective amounts of rHSA according to the present invention is 300 microliters-5 mL, and preferably no more than 2 mL; below 300 microliters, the rHSA becomes a gel and does not preserve the tissue for the two year time frame; such low amounts of rHSA were not possible prior to this invention because the appropriate packaging system to hold such a small amount was not yet developed), and (3) no sponge-like material is required within the packaging to keep the stored tissue moist (this is due also, in part, to the funnel design of the packaging—the funnel design allows the volume of rHSA to be as small as possible while also providing an opening sufficiently large for ease of handling, processing, and packaging). All three advantages noted above are at least cost-saving advantages (e.g., less mass enables a faster irradiation time and with less of a dose, whereas higher energy electron beams and/or slower conveyer speeds are required for penetrating a larger mass/volume/thickness and also increases the potential for negative effects of the irradiation process). In addition, the preservation media may contain a cryoprotectant and clarity enhancer. The preservation media may further comprise other tissue protectants known in the art without limitation but such as cryoprotectants, oxidation protectants, radical scavengers, and protein denaturation protectants.

9. The corneal tissue is then placed in a second/outer pouch further protecting the inner packaging for sterilization, storage, transport, and transplantation 107.
10. If/when transport to an EBS facility is required, the tissue-in-custom-container may be transported on ice to keep the pre-sterilized grafts cool and to retard deterioration, especially to protect from bioburden increases, and to maintain clarity, pliability, and consistency. It is noted that although the tissue may be on ice at this point in the process, it is not frozen.
11. Electron beam irradiation of the corneal tissue 108 occurs at ambient temperature up to 7 days (preferably within 2 days) after arrival, as long as the tissue is maintained at refrigeration temperatures. It is preferred to have the tissue irradiated within 72 hours of thawing, if the tissue is frozen prior to sterilization. The tissue remains refrigerated during the thawing time. The reason for such maintained refrigeration is to ensure the bioburden does not increase significantly in which case the irradiation can be ineffective. Sterilization time can be 25 minutes or less, preferably ranging from 2 minutes to 25 minutes, to complete once a sample is loaded onto the electron beam conveyor system. During electron irradiation the tissue receives 5, 10, 15, 20 or 25 kilogrey (kGy) of electronic beam irradiation measured as a tissue internal dose by methods well known to those skilled in the art. Using two electron beam accelerators opposite from each other and offset gives the shortest time for the irradiation to be completed, thus minimizing temperature increase. An alternative solution when having access to only one accelerator is to have the conveyor system turn the container so that the other side may be irradiated—a process that takes additional time and that can contribute to temperature rise. Keeping the temperature rise to a minimum during sterilization is optimized to ensure that the transparency, pliability, and consistency of the collagenous tissue is not compromised, while providing an SAL of $10^{-6}$.
12. The package is then shipped to and stored at the eye bank at an ambient temperature 109.
13. The corneal tissue is held in quarantine until its safety is verified by a Certificate of Irradiation, based on dose mapping and validation. Corneal tissues may also be subject to other quality assurance measures, such as but not limited to clarity and package integrity inspection. The process described above creates a tissue storable for a validated 2-year shelf life. The packaging and tissue is not refrozen or refrigerated after sterilization, as each sample is preserved and sterile and remains as such without the need for lower storage temperatures.

The illustrative examples below demonstrate exemplary applications of the inventive technology:

Example 1: Toxicological Study

The MatTek EpiOcular™, a cultured, 3-dimensional in vitro human cell-based corneal model, was used to evaluate the potential of test articles to cause toxicity and/or ocular irritation of the new storage media after electron beam irradiation. The objective of this study was to assess the ocular irritation potential of the novel tissue storage media recombinant human albumin and compare it to 1). a known irritant, benzalkonium chloride and 2). the comparable product being offered for allograft transplants stored in pooled/processed human albumin. A positive control, 1% benzalkonium chloride (BC), was effective, reducing cell viability over three time periods. Therefore the positive control, 1% BC, is categorized as a severe irritant. Exposure of ocular tissues to rHSA had no effect on tissue viability up to and including the 300 min exposure. In addition, rHSA exposure did not induce a substantial release of IL-1α above what was observed with the negative control except at one of the exposure times, 10 minutes. This response quickly receded, however. Therefore, rHSA is categorized as a non/minimal irritant. Exposure of ocular tissues to control pooled/processed human albumin had no effect on tissue viability up to and including the 300 min exposure. In addition, control human albumin exposure did not induce a substantial release of IL-1α above what was observed with the negative control except at one of the exposure times, 10 minutes. This response quickly receded, however. Therefore, control human albumin is categorized as a non/minimal irritant.

Example 2: Irradiated Tissue Clarity

A pre and post-treatment comparison of 18 donor corneas was performed. The clarity of each tissue was evaluated and compared using dark field microscopy. Each cornea served as its own control, first as fresh tissue and then again following electron beam irradiation. Overall, there was a net change in clarity of −2.7% following treatment, p=0.002. The maintenance of corneal clarity utilizing this new processing and sterilization regimen is sufficient for clinical use.

Example 3: Irradiated Tissue Histology

Corneal tissues subjected to the sterilization process were fixed in formalin and evaluated by an ocular pathologist after hematoxylin and eosin staining. The ocular pathological examinations were masked to fact that the tissue was subjected to a novel sterilization process. Tissue was deemed normal by histological examination. There were no identified differences between electron beam irradiated tissue and normal cornea.

Example 4: Irradiated Tissue Sterility

Corneas are irradiated in a validated process according to standards of the American National Standards Institute (ANSI) and the International Standards Organization (ISO). These standards provide detailed guides for validating a process in order to make a sterility claim. The method used for this process is as follows. For biologicals, tissue is tested for bioburden levels and based on bioburden an absorbed irradiation dose in kilograys (kGy) is recommended by ISO standards. Tissue is then processed according to the standard protocol and then irradiated at $\frac{1}{10}^{th}$ the dose recommended which is the verification dose. Ten tissue samples are then tested for sterility. No growth or growth beyond permissible limits in the tissue samples irradiated at the verification dose indicates that sterility can be assured at the actual sterility dose. Tissue irradiated in future runs cannot be released without documented evidence from the irradiation facility that the required dose has been achieved.

Fifty (50) specimens were tested for anaerobes, aerobes and fast growing fungi. All corneal specimens tested were found to have no growth. Bacteriostasis and fungistasis studies were also performed to establish the suitability of the growth medias used in the study.

Another unexpected result, based on the fact that current rHSA vendors claim that reconstituted rHSA will degrade in several months if not stored at −20 degrees Celsius or below. The present invention and experiment results show that preservation and retention of transplant quality for 2 years or more is possible regardless of any actual changes that might occur over time. This is because either changes or other degradation occur without affecting process of the present invention, or alternatively because the present process stops or at least retards the changes and/or degradation. One reason for the present process to blunt any change/degradation is that the irradiation (e-beam) completely sterilizes the package, which eliminates the possibility of degradation by microbial contamination.

Example 5: Minimal Sufficient rHSA Concentration for Storage in Packaging

Pouches according to the present invention are filled with varying amounts of rHSA (see FIG. 3)—control group (i.e., 3 drops rHSA, by dropper) 301, 150 μL (by micropipette) 302, 200 μL 303, 300 μL 304, and 400 μL 305. Each sample is incubated at 42 degrees Celsius for 4 months (equivalent of 1 year at ambient temperature) (see FIG. 3). Additionally, others tissues processed, packaged, and stored for 10 months at room temperature, filled with either 200 μL rHSA or 400 μL rHSA, were moved from their ambient temperature storage for 10 months to a storage at 42 degrees Celsius for 4 months (see FIGS. 4-5). The results showed that the rHSA in each sample turned yellow, the rHSA in samples 301-303 began to solidify into a gel-like substance, and the rHSA in samples 304-305 remained a liquid while also maintaining the best quality tissue, as is preferred. Liquid is preferred because it maintains a moistness of the tissue being stored and maintains tissue consistency, pliability, clarity, etc. Samples having 400 microliters of rHSA resulted in high quality tissues as well as non-gel-like media (samples with 300 microliters rHSA showed statistically comparable results; however, additional samples having less than 300 microliters still showed gel-like properties after storage). The overall experiment showed that adding more rHSA to the packaging will extend the useful life of tissue processed, packaged, and stored as described herein, with the minimum sufficient value being 300 microliters. It is noted that raising the amount of rHSA per sample directly impacts the cost associated with the process described herein. It is thus noted further that rHSA in the amount of about 20% to about 35% by weight is also applicable to the present invention; nonetheless, 20% rHSA by weight is preferred. Higher concentrations of rHSA may stain the tissue to an unacceptable level and/or cause the tissue to shrink.

The specific embodiments described herein are intended to further explain the best mode known for practicing the disclosure and to enable others skilled in the art to utilize the disclosure in such, or other, embodiments and with various modifications required by the particular applications or uses of the present disclosure. The specific techniques, conditions, materials, and proportions set forth to illustrate the principles and practice of the invention are exemplary only and should not be taken as limiting the scope of the invention. It is intended that the appended claims be construed to include alternative embodiments to the extent permitted by the prior art.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. A method for preparation and storage of mammalian collagen tissue for transplantation or implantation into a recipient, comprising:

receiving a mammalian collagen tissue, said tissue being sufficiently clear based on an evaluation, packaging said mammalian collagen tissue with a medium in a first pouch container said first pouch container comprising a funnel shaped reservoir, said medium comprising at least 20% recombinant human serum albumin by weight, said medium maintaining said tissue's consistency, said tissue's pliability, and said tissue's clarity, said medium having a total volume of up to 5 milliliters, wherein said mammalian collagen tissue is partially submerged in said medium and remains partially submerged in said medium, packaging said tissue in said medium in said first container within a second pouch container, electron beam sterilizing said mammalian collagen tissue packaged in said first and second pouch containers, and storing said sterilized mammalian collagen tissue packaged in said first and second pouch containers at an ambient temperature for up to two years in an absence of any change to said consistency, said clarity, and said pliability, wherein the first and second pouch containers comprise clear protective barrier films, said films being aluminum oxide coated polyester-based films.

2. The method of claim 1, wherein said mammalian collagen tissue is a human collagen tissue.

3. The method of claim 2, wherein said human collagen tissue is a corneal tissue.

4. The method of claim 3, wherein said corneal tissue is a corneal stromal matrix.

5. The method of claim 1, wherein said first pouch container further contains an absorbent material.

6. The method of claim 1, wherein said electron beam sterilization is conducted at or below an ambient temperature.

7. The method of claim 1, wherein said electron beam sterilization delivers an electron beam sufficient for a tissue internal dose of 15 to 25 kilogray (kGy) for a period no greater than 25 minutes.

8. The method of claim 1, wherein a transparency of the first and second pouch containers does not change after said electron beam sterilization.

9. The method of claim 1, wherein said first pouch container is clear.

10. The method of claim 1, further comprising splitting a single one of said received mammalian collagen tissue into four (4) or more grafts, each graft forming a separate unit to be individually packaged in said packaging step.

11. The method of claim 1, further comprising:
freeze-storing said tissue packaged within said first and second containers at a temperature of −40 to −85 degrees Celsius, said freeze-storing occurring after said packaging and before said sterilization.

12. The method of claim 11, wherein said electron beam sterilizing comprises irradiating a plurality of thawed tissues, each thawed tissue comprising said tissue packaged within said first and said second pouch containers.

13. The method of claim 12, wherein said plurality of thawed tissues are sterilized in a single file arrangement.

14. The method of claim 1, wherein said first pouch container or said second pouch container further comprise foil.

15. The method of claim 1, wherein said medium having a total volume of about 300 microliters.

* * * * *